(12) United States Patent
Kikawa et al.

(10) Patent No.: US 7,643,154 B2
(45) Date of Patent: Jan. 5, 2010

(54) OPTICAL IMAGE MEASUREMENT DEVICE

(75) Inventors: Tsutomu Kikawa, Tokyo (JP); Hiroaki Okada, Tokyo (JP); Takefumi Hayashi, Tokyo (JP); Hisashi Tsukada, Tokyo (JP); Yasufumi Fukuma, Tokyo (JP)

(73) Assignee: Kabushiki Kaisha Topcon, Itabashi-ku (JP)

( * ) Notice: Subject to any disclaimer, the term of this patent is extended or adjusted under 35 U.S.C. 154(b) by 111 days.

(21) Appl. No.: 11/961,195

(22) Filed: Dec. 20, 2007

(65) Prior Publication Data

US 2008/0151256 A1 Jun. 26, 2008

(30) Foreign Application Priority Data

Dec. 26, 2006 (JP) .............................. 2006-349880

(51) Int. Cl.
*G01B 11/02* (2006.01)
(52) U.S. Cl. ...................................... 356/497
(58) Field of Classification Search ................ 356/479, 356/497
See application file for complete search history.

(56) References Cited

U.S. PATENT DOCUMENTS

2005/0140984 A1* 6/2005 Hitzenberger ............... 356/497

FOREIGN PATENT DOCUMENTS

| DE | 43 09 056 | 9/1994 |
| JP | 11-325849 | 11/1999 |
| JP | 2003-000543 | 1/2003 |

* cited by examiner

*Primary Examiner*—Tarifur Chowdhury
*Assistant Examiner*—Jonathon D Cook
(74) *Attorney, Agent, or Firm*—Edwards Angell Palmer & Dodge LLP

(57) ABSTRACT

An optical image measurement device comprises: a light source configured to emit a low-coherence light; an interference-light generator configured to generate an interference light, by splitting the low-coherence light into a signal light and a reference light, and superimposing the signal light passed through a measurement object and the reference light passed through a reference object; a changer configured to change a difference in optical path length; a detector configured to detect the interference light; an image forming part configured to form an image of the measurement object within a predetermined frame based on the result of the detection; an analyzer configured to analyze the image, and specify a position of the image within the frame; and a controller configured to control the changer based on the specified position to change the difference so that an image newly formed is placed in a predetermined position within the frame.

5 Claims, 16 Drawing Sheets

OPTICAL IMAGE MEASUREMENT DEVICE

BACKGROUND OF THE INVENTION

1. Field of the Invention

The present invention relates to an optical image measurement device configured to apply a light beam to a measurement object and form an image of the surface morphology or internal morphology of the measurement object by using a reflected light or a transmitted light.

2. Description of the Related Art

In recent years, attention has been focused on an optical image measurement technology of forming an image showing the surface morphology or internal morphology of a measurement object by using a light beam from a laser light source or the like. Because this optical image measurement technology does not have invasiveness to human bodies unlike an X-ray CT device, it is particularly expected to further use this technology in the medical field.

Japanese Unexamined Patent Application Publication JP-A 11-325849 discloses an optical image measurement device having a configuration that: a measuring arm scans an object through a rotary deflection mirror (Galvano mirror); a reference mirror is disposed to a reference arm; an interferometer is used at the outlet so that the intensity of light appearing from interference of light fluxes from the measuring arm and the reference arm is analyzed by a spectrometer; and a device gradually changing the light flux phase of the reference light in non-continuous values is disposed to the reference arm.

The optical image measurement device of JP-A 11-325849 uses a method of so-called "Fourier Domain Optical Coherence Tomography (OCT)" based on technology of German Patent Application Publication DE4309056A1. That is to say, a beam of a low-coherence light is applied to a measurement object, the spectrum intensity distribution of a reflected light is obtained, and the obtained distribution is subjected to Fourier conversion, whereby an image of the morphology of the measurement object in a depth direction (z-direction) is formed.

Furthermore, the optical image measurement device described in JP-A 11-325849 is provided with a Galvano mirror that scans with an optical beam (signal light), whereby it is possible to form an image of a desired measurement region of a measurement object. Because this optical image measurement device is configured to scan with a light beam only in one direction (x-direction) orthogonal to the z-direction, a formed image is a 2-dimensional cross-sectional image of the depth direction (z-direction) along the light beam scanning direction (x-direction).

Besides, Japanese Unexamined Patent Application Publication JP-A 2003-543 discloses a configuration in which the aforementioned optical image measurement device is applied to the field of ophthalmology.

An optical image measurement device forms an image by measuring a depth almost the same as the length of a reference arm (the optical path length of a reference light). Therefore, in order to capture an image of a desired depth position, it is necessary to place a reference mirror at a position corresponding to the depth position. Considering the use of a low-coherence light, alignment of the reference mirror, namely, alignment of the measurement position in the depth direction must be conducted precisely.

Further, in an optical image measurement device, the measurement sensitivity is the most favorable at a depth position that coincides with the optical path length of the reference light (origin of the z-direction), and the measurement sensitivity becomes lower as it is distant from the origin. Also from this aspect, it is understood that alignment of the measurement position in the depth direction needs precision.

The alignment of a measurement position in the depth direction is important in a case where a measurement object moves in the depth direction during measurement, such as a case where measurement of a living body is performed. That is, in a case where a measurement object moves in the depth direction during measurement, there is the fear that an image in a target depth position cannot be captured. For example, even if the alignment of a measurement position in the depth direction is performed in advance, the measurement position is displaced in the depth direction because of movement of a measurement object, so that an image in a target depth position cannot be captured. Even if an image in a target depth position can be captured, the target depth position moves away from an original point of the Z-direction and measurement sensitivity lowers thereby, so that there is the fear that only an image of low accuracy can be captured.

Further, for example, at the time of capture of images at a plurality of sites of a fundus oculi, a measurement position in the depth direction of each of the sites may be displaced because the surface of the fundus oculi (retina) is a curved face. For example, between an image captured at the center of the fundus oculi and an image captured at a site away from the center, there is a difference in measurement position in the depth direction, whereby the positions of the images within a frame are displaced from each other. This problem generally arises in not only capture of images of the fundus oculi but also capture of images of any measurement object such that measurement positions in the depth direction vary depending on sites.

SUMMARY OF THE INVENTION

The present invention was made in order to solve the aforementioned problem. An object of the present invention is to provide an optical image measurement device capable of capturing an image of a target depth position of a measurement object.

In an aspect of the present invention, an optical image measurement device comprises: a light source configured to emit a low-coherence light; an interference-light generator configured to generate an interference light, by splitting the emitted low-coherence light into a signal light heading toward a measurement object and a reference light heading toward a reference object, and superimposing the signal light passed through the measurement object and the reference light passed through the reference object; a changer configured to change a difference in optical path length between the signal light and the reference light; a detector configured to detect the generated interference light; an image forming part configured to form an image of the measurement object within a predetermined frame based on the result of the detection by the detector; an analyzer configured to analyze the formed image, and specify a position of the image within the predetermined frame; and a controller configured to control the changer based on the specified position to change the difference in optical path length so that an image of the measurement object newly formed by the image forming part is placed in a predetermined position within the predetermined frame.

BRIEF DESCRIPTION OF THE DRAWINGS

FIG. 8A shows one example of a scanning pattern of the signal light when a fundus oculi is seen from the incident side of the signal light to an eye. FIG. 8B shows one example of an arrangement pattern of scanning points on each scanning line.

DETAILED DESCRIPTION OF THE PREFERRED EMBODIMENT

Figure 1:
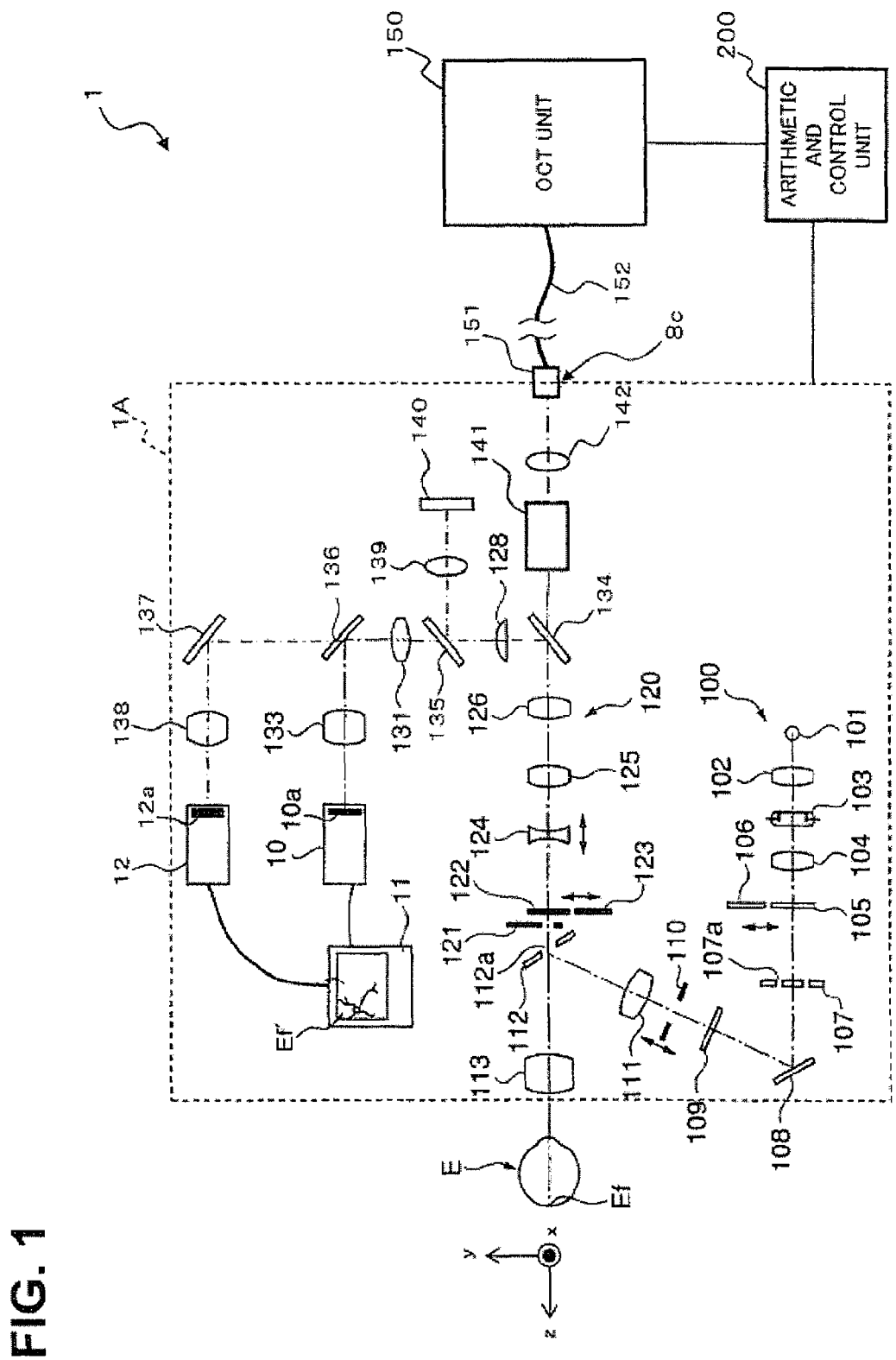
FIG. 1 is a schematic configuration diagram showing one example of the entire configuration in a preferred embodiment of a device related to the present invention.

One example of a preferred embodiment of an optical image measurement device according to the present invention will be described in detail referring to the drawings.

[Configuration of Device]

Figure 2:
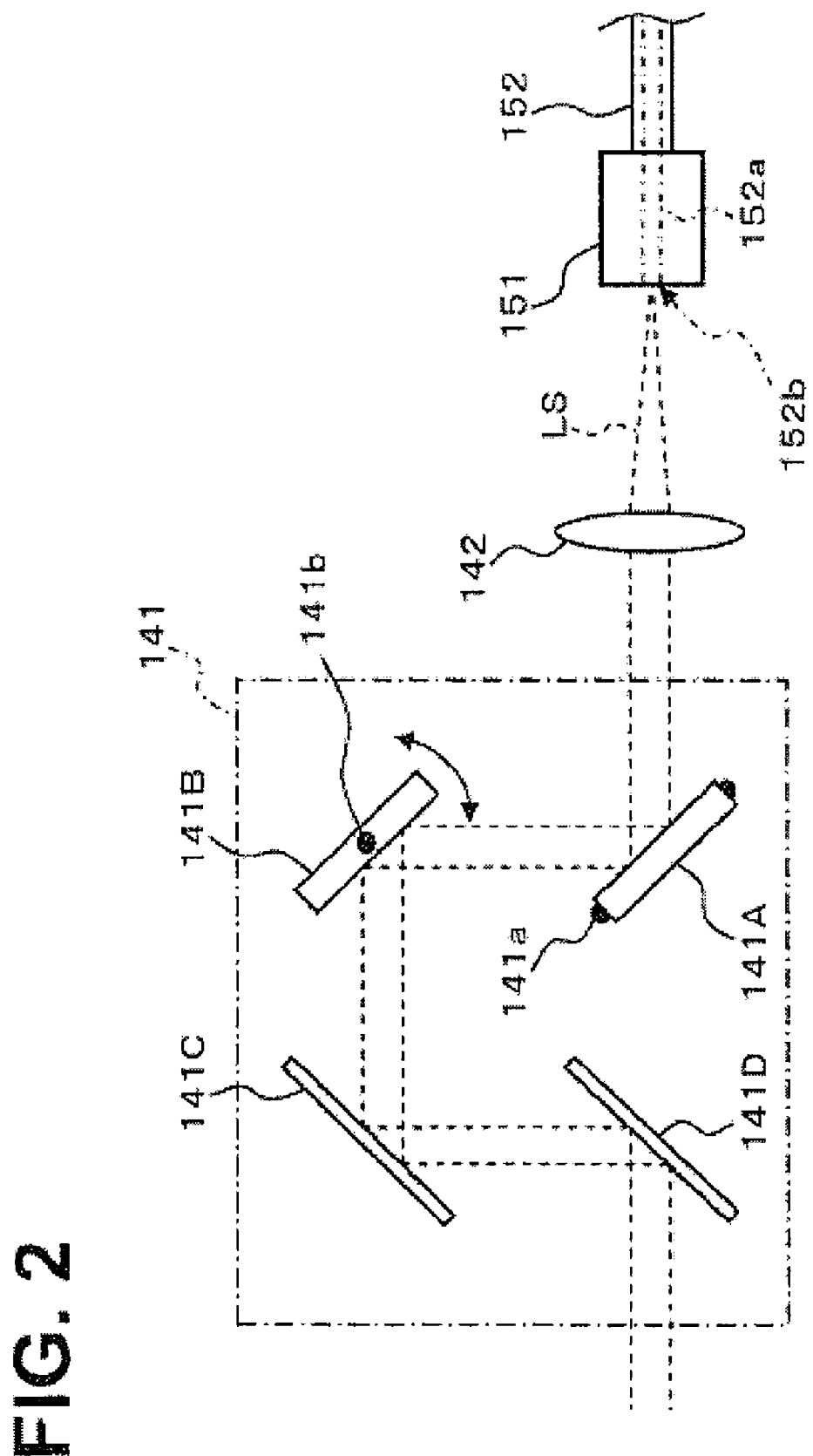
FIG. 2 is a schematic configuration diagram showing one example of the configuration of a scan unit installed in a retinal camera unit in the preferred embodiment of the device related to the present invention.
Figure 3:
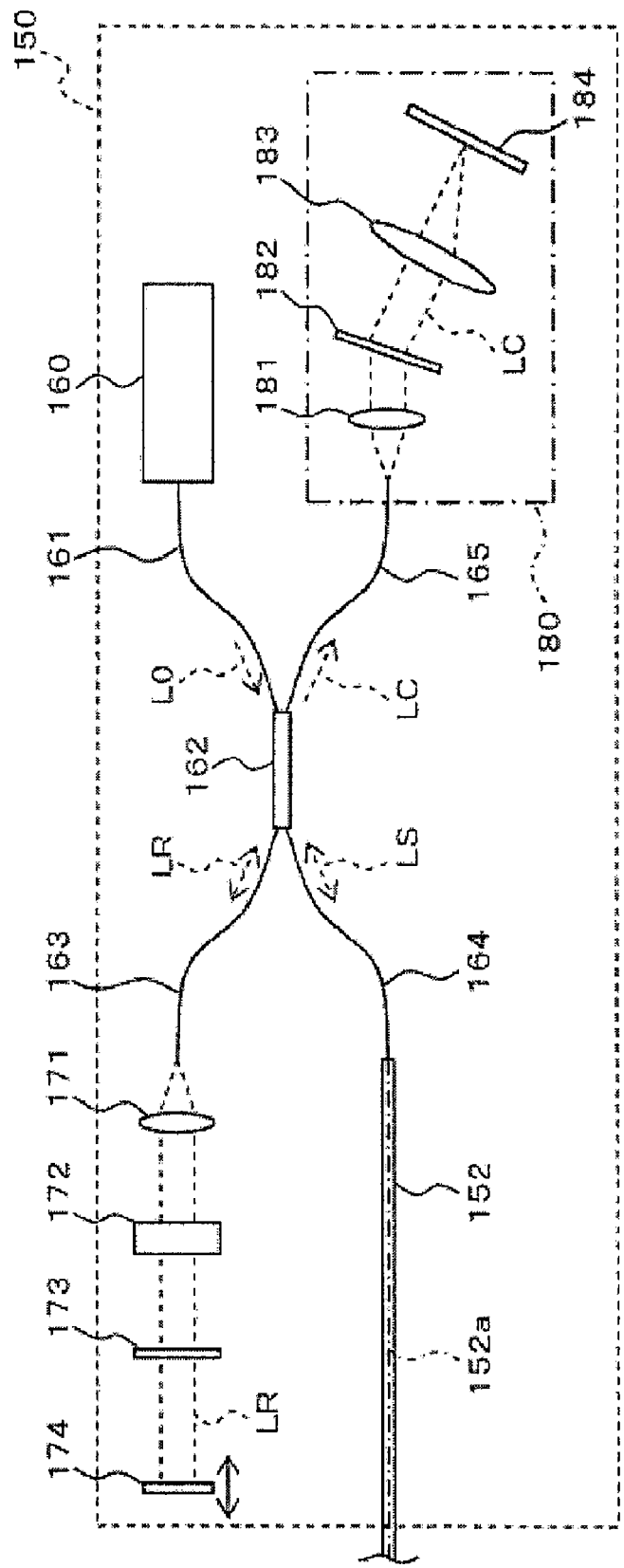
FIG. 3 is a schematic configuration diagram showing one example of the configuration of an OCT unit in the preferred embodiment of the device related to the present invention.
Figure 4:
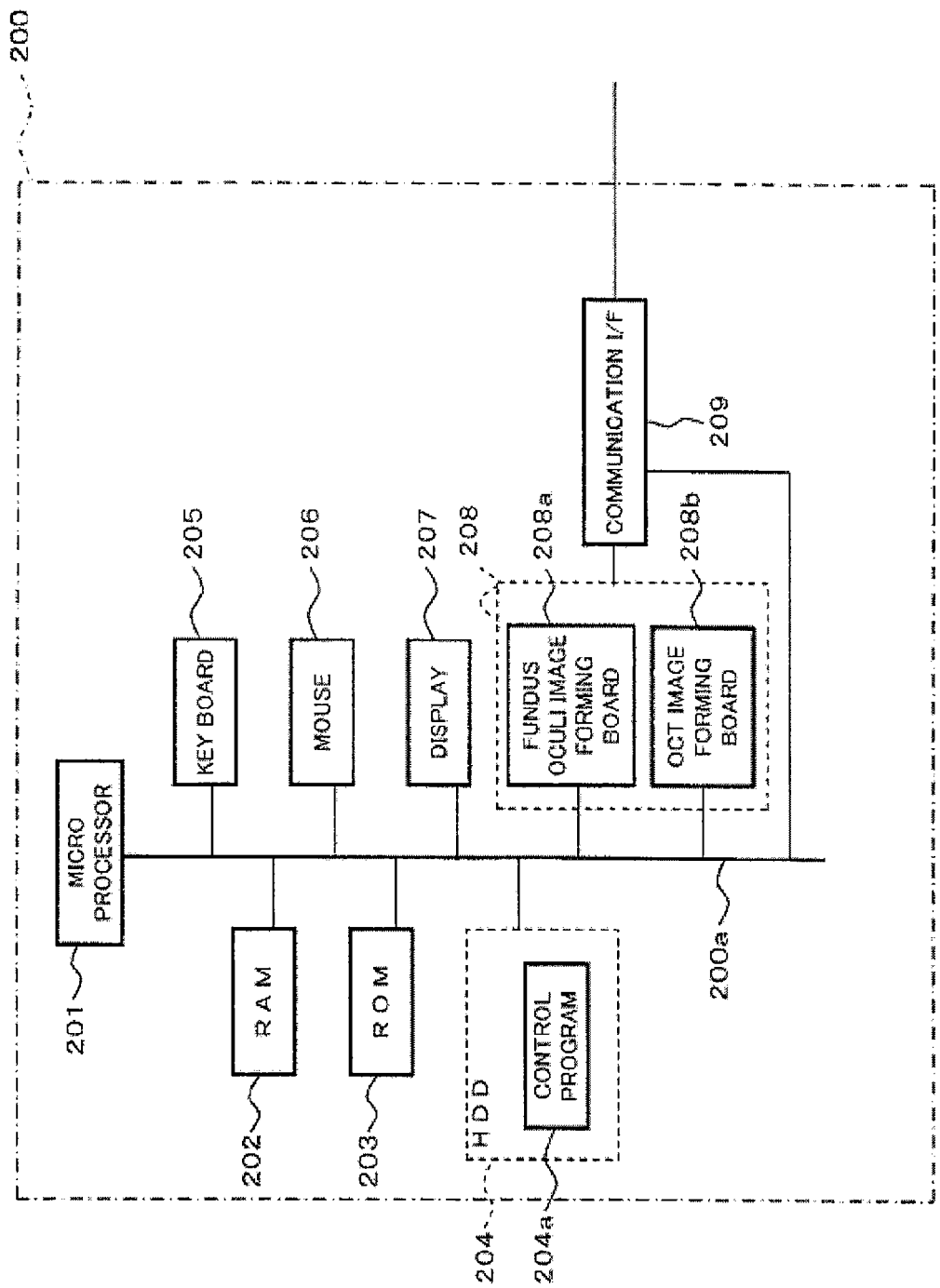
FIG. 4 is a schematic block diagram showing one example of the hardware configuration of an arithmetic control unit in the preferred embodiment of the device related to the present invention.
Figure 5:
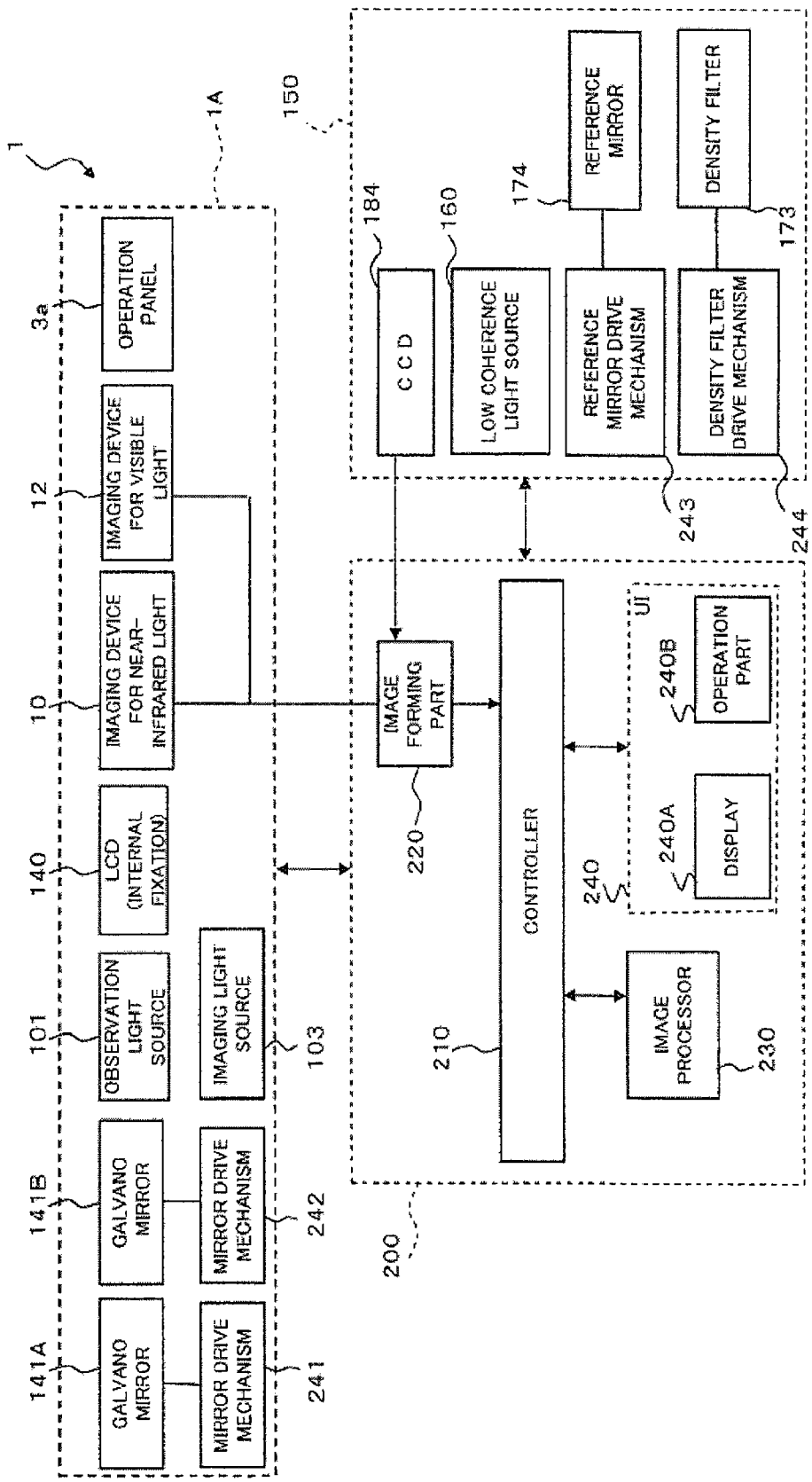
FIG. 5 is a schematic block diagram showing one example of the configuration of a control system in the preferred embodiment of the device related to the present invention.
Figure 6:
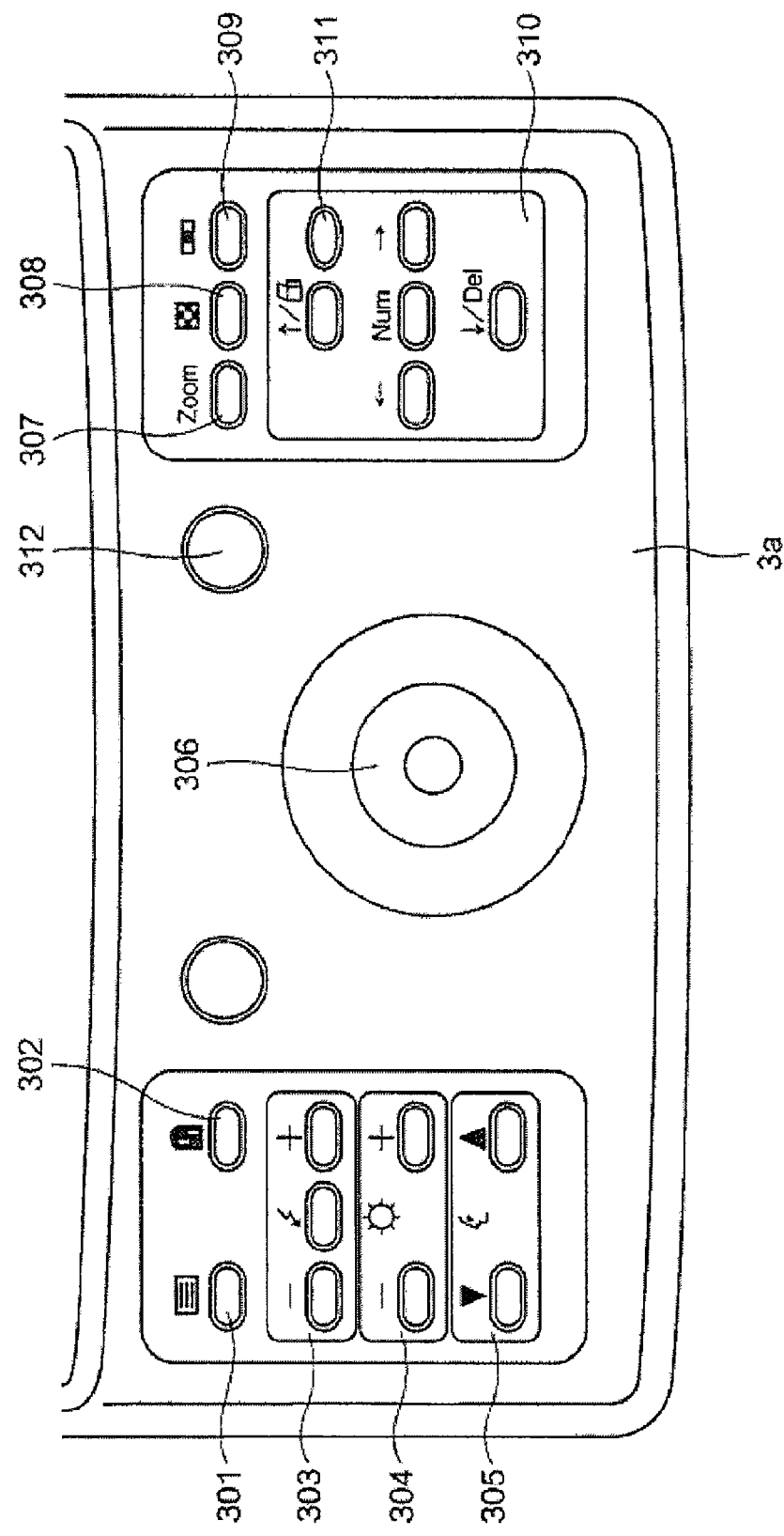
FIG. 6 is a schematic view showing one example of the appearance of an operation panel in the preferred embodiment of the device related to the present invention.
Figure 7:
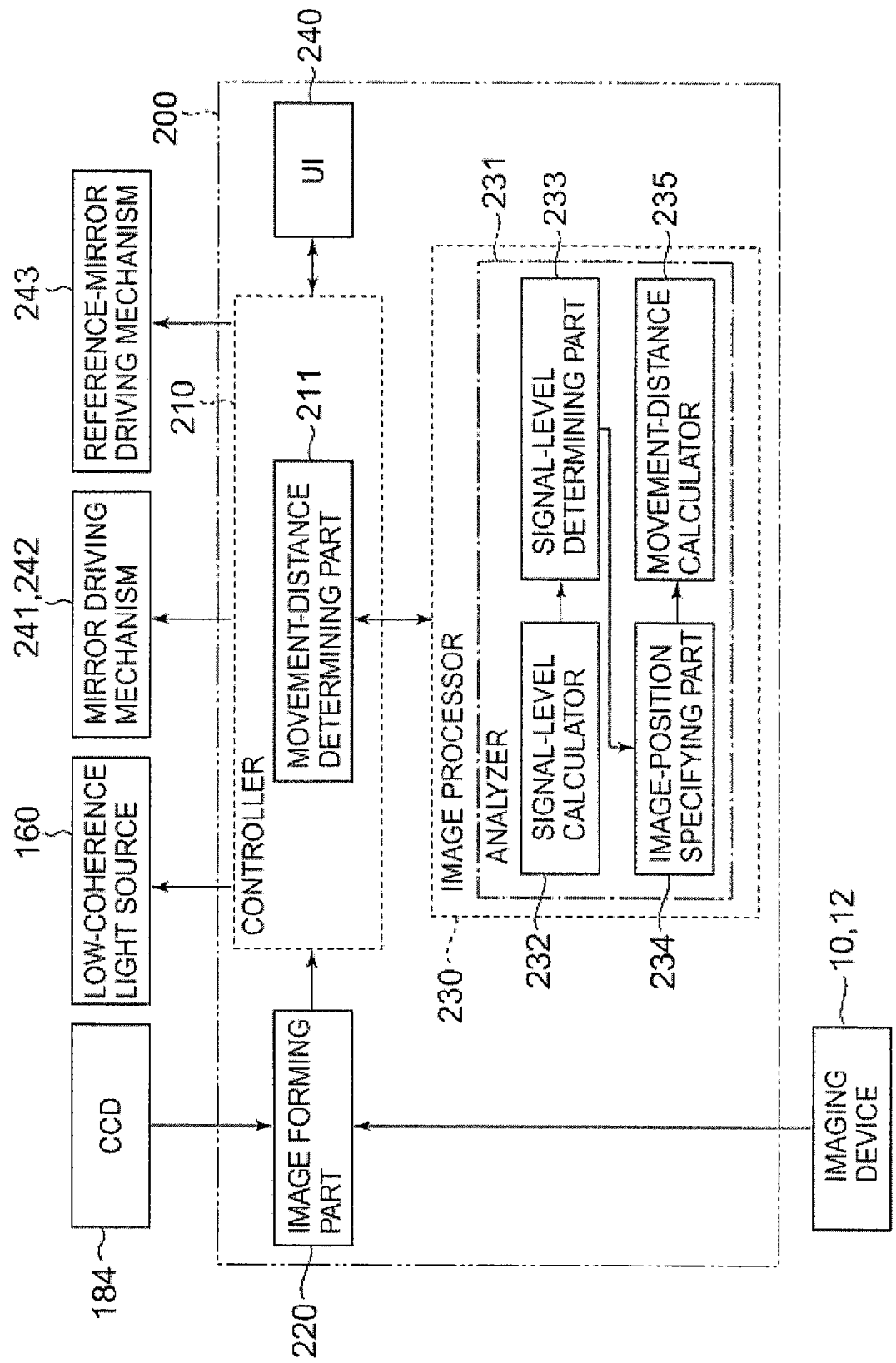
FIG. 7 is a schematic block diagram showing one example of the functional configuration of the arithmetic control unit in the preferred embodiment of the device related to the present invention.

First, referring to FIGS. 1 through 7, the configuration of the optical image measurement device according to a first embodiment of the present invention will be described. FIG. 1 shows one example of the entire configuration of a fundus oculi observation device 1 having a function as the optical image measurement device according to this embodiment. FIG. 2 shows one example of the configuration of a scan unit 141 in a retinal camera unit 1A. FIG. 3 shows one example of the configuration of an OCT unit 150. FIG. 4 shows one example of the hardware configuration of an arithmetic control unit 200. FIG. 5 shows one example of the configuration of a control system of the fundus oculi observation device 1. FIG. 6 shows one example of the configuration of an operation panel 3a disposed to the retinal camera unit 1A. FIG. 7 shows one example of the configuration of a control system of the arithmetic control unit 200.

[Entire Configuration]

The fundus oculi observation device 1 related to this embodiment comprises a retinal camera unit 1A, an OCT unit 150, and an arithmetic control unit 200 as shown in FIG. 1. The retinal camera unit 1A has almost the same optical system as the conventional retinal cameras for photographing 2-dimensional images of the fundus oculi surface. The OCT unit 150 houses an optical system that functions as an optical image measurement device. The arithmetic control unit 200 is equipped with a computer for executing various types of arithmetic processes, control processes, or the like. To the OCT unit 150, one end of a connection line 152 is attached. A connector part 151 for connecting the connection line 152 to the retinal camera unit 1A is attached to the other end of the connection line 152. A conductive optical fiber runs through inside the connection line 152. Thus, the OCT unit 150 and the retinal camera unit 1A are optically connected via the connection line 152.

Configuration of Retinal Camera Unit

The retinal camera unit 1A is used for forming a 2-dimensional image of the surface of a fundus oculi of an eye, based on optically obtained data (data detected by the imaging devices 10 and 12). Herein, the "2-dimensional image of the surface of the fundus oculi" refers to a color or monochrome image of the surface of the fundus oculi having been photographed, a fluorescent image (a fluorescein angiography image, an indocyanine green fluorescent image, etc.), and the like. As well as the conventional retinal camera, the retinal camera unit 1A is provided with an illumination optical system 100 that illuminates a fundus oculi Ef of an eye E, and an imaging optical system 120 that guides the fundus oculi reflection light of the illumination light to the imaging device 10.

Although the details will be described later, the imaging device 10 in the imaging optical system 120 of this embodiment detects the illumination light having a wavelength in the near-infrared region. Moreover, this imaging optical system 120 is further provided with the imaging device 12 for detecting the illumination light having a wavelength in the visible region. Moreover, this imaging optical system 120 guides a signal light coming from the OCT unit 150 to the fundus oculi Ef, and guides the signal light passed through the fundus oculi Ef to the OCT unit 150.

The illumination optical system 100 comprises: an observation light source 101; a condenser lens 102; an imaging light source 103; a condenser lens 104; exciter filters 105 and 106; a ring transparent plate 107; a mirror 108; an LCD (Liquid Crystal Display) 109; an illumination diaphragm 110; a relay lens 111; an aperture mirror 112; and an objective lens 113.

The observation light source 101 emits an illumination light having a wavelength of the visible region included in a range of, for example, about 400 nm thorough 700 nm. Moreover, the imaging light source 103 emits an illumination light having a wavelength of the near-infrared region included in a range of, for example, about 700 nm through 800 nm. The near-infrared light emitted from this imaging light source 103 is set so as to have a shorter wavelength than the light used by the OCT unit 150 (described later).

Further, the imaging optical system 120 comprises: an objective lens 113; an aperture mirror 112 (an aperture 112a thereof); an imaging diaphragm 121; barrier filters 122 and 123; a variable magnifying lens 124; a relay lens 125; an imaging lens 126; a dichroic mirror 134; a field lens 128; a half mirror 135; a relay lens 131; a dichroic mirror 136; an imaging lens 133; the imaging device 10 (image pick-up element 10a); a reflection mirror 137; an imaging lens 138; the imaging device 12 (image pick-up element 12a); a lens 139; and an LCD 140.

The dichroic mirror 134 is configured to reflect the fundus oculi reflection light (having a wavelength included in a range of about 400 nm through 800 nm) of the illumination light from the illumination optical system 100, and transmit a signal light LS (having a wavelength included in a range of, for example, about 800 nm through 900 nm; described later) from the OCT unit 150.

Further, the dichroic mirror 136 is configured to transmit the illumination light having a wavelength of the visible region from the illumination optical system 100 (a visible light having a wavelength of about 400 nm through 700 nm emitted from the observation light source 101), and reflect the illumination light having a wavelength of the near-infrared region (a near-infrared light having a wavelength of about 700 nm through 800 nm emitted from the imaging light source 103).

On the LCD 140, a fixation target (internal fixation target) or the like for fixing the eye E is displayed. The light from this LCD 140 is reflected by the half mirror 135 after being converged by the lens 139, and is reflected by the dichroic mirror 136 through the field lens 128. Then, the light passes through the imaging lens 126, the relay lens 125, the variable magnifying lens 124, the aperture mirror 112 (aperture 112a thereof), the objective lens 113 and the like, and enters the eye E. Consequently, an internal fixation target or the like is projected in the fundus oculi Ef of the eye E.

The image pick-up element 10a is an image pick-up element such as a CCD (Charge Coupled Device) and a CMOS (Complementary metal Oxide Semiconductor) installed in the imaging device 10 such as a TV camera, and is particularly used for detecting light having a wavelength of the near-infrared region. In other words, the imaging device 10 is an infrared TV camera for detecting near-infrared light. The imaging device 10 outputs video signals as a result of detection of the near-infrared light.

A touch panel monitor 11 displays a 2-dimensional image (a fundus oculi image Ef') of the surface of the fundus oculi Ef, based on the video signals. The video signals are sent to the arithmetic control unit 200, and the fundus oculi image is displayed on the display (described later).

At the time of imaging of the fundus oculi by the imaging device 10, for example, the illumination light emitted from the imaging light source 103 of the illumination optical system 100 and having a wavelength of the near-infrared region is used.

On the other hand, the image pick-up element 12a is an image pick-up element such as a CCD and a CMOS installed in the imaging device 12 such as a TV camera, and is particularly used for detecting light having a wavelength of the visible region (that is, the imaging device 12 is a TV camera for detecting visible light). The imaging device 12 outputs video signals as a result of detection of the visible light.

The touch panel monitor 11 displays a 2-dimensional image (fundus oculi image Ef') of the surface of the fundus oculi Ef, based on the video signals. The video signals are sent to the arithmetic control unit 200, and the fundus oculi image Ef' is displayed on the display (described later).

At the time of imaging of the fundus oculi by the imaging device 12, for example, the illumination light emitted from the observation light source 101 of the illumination optical system 100 and having a wavelength of the visible region is used.

The retinal camera unit 1A is provided with a scan unit 141 and a lens 142. The scan unit 141 includes a component for scanning at an application position of the fundus oculi Ef with light emitted from the OCT unit (signal light LS; described later). The scan unit 141 functions as one example of the "scanner" of the present invention.

The lens 142 makes the signal light LS guided from the OCT unit 150 through the connection line 152 enter the scan unit 141 in the form of a parallel light flux. Moreover, the lens 142 acts so as to converge the fundus oculi reflection light of the signal light LS passed through the scan unit 141.

FIG. 2 shows one example of a specific configuration of the scan unit 141. The scan unit 141 comprises Galvano mirrors 141A and 141B, and reflection mirrors 141C and 141D.

The Galvano mirrors 141A and 141B are reflection mirrors disposed so as to be rotatable about rotary shafts 141a and 141b, respectively. The Galvano mirrors 141A and 141B are rotated about the rotary shafts 141a and 141b, respectively, by a drive mechanism described later (mirror drive mechanisms 241 and 242 shown in FIG. 5), whereby the orientations of reflection surfaces thereof (faces reflecting the signal light LS), namely, the positions of the Galvano mirrors 141A and 141B are changed, respectively.

The rotary shafts 141a and 141b are arranged so as to be orthogonal to each other. In FIG. 2, the rotary shaft 141a of the Galvano mirror 141A is arranged in parallel to the paper face of FIG. 2, whereas the rotary shaft 141b of the Galvano mirror 141B is arranged so as to be orthogonal to the paper face of FIG. 2.

That is to say, the Galvano mirror 141B is formed so as to be rotatable in the directions indicated by an arrow pointing in both directions in FIG. 2, whereas the Galvano mirror 141A is formed so as to be rotatable in the directions orthogonal to the arrow pointing in both the directions. Consequently, the pair of Galvano mirrors 141A and 141B act so as to change the reflecting directions of the signal light LS to directions orthogonal to each other. As seen from FIGS. 1 and 2, scan with the signal light LS is performed in the x direction when the Galvano mirror 141A is rotated, and scan with the signal light LS is performed in the y direction when the Galvano mirror 141B is rotated.

The signal lights LS reflected by the Galvano mirrors 141A and 141B are reflected by reflection mirrors 141C and 141D, thereby traveling in the same directions as having entered into the Galvano mirror 141A.

As described before, the conductive optical fiber 152a runs through the inside of the connection line 152, and an end face 152b of the optical fiber 152a is arranged facing the lens 142. The signal light LS emitted from this end face 152b travels while expanding its beam diameter toward the lens 142. The light is converged into a parallel light flux by this lens 142. On the contrary, the signal light LS passed through the fundus oculi Ef is converged toward the end face 152b by the lens 142, and guided to the optical fiber 152a.

Configuration of OCT Unit

Next, the configuration of the OCT unit 150 will be described referring to FIG. 3. The OCT unit 150 is a device configured to form a tomographic image of the fundus oculi based on optically obtained data (data detected by a CCD 184 described later).

The OCT unit 150 has almost the same optical system as the conventional optical image measurement device. That is, the OCT unit 150 has: an interferometer that splits the light emitted from the light source into a reference light and a signal light and generates interference-light by superposing the reference light passed through a reference object and the signal light passed through a measurement object (fundus oculi Ef); and a part configured to detect this interference-light and output signals as the result of the detection (detection signals) toward the arithmetic control unit 200. The arithmetic control unit 200 forms a tomographic image of the measurement object (fundus oculi Ef), by analyzing the detection signals.

A low-coherence light source 160 is composed of a broadband light source, such as a super luminescent diode (SLD) and a light emitting diode (LED), configured to emit a low-coherence light LO. This low-coherence light L0 is, for example, a light that has a wavelength of the near-infrared region and has a time-wise coherence length of approximately several tens of micrometers. The low-coherence light source 160 corresponds to one example of the "light source" of the present invention.

The low-coherence light L0 has a longer wavelength than the illumination light (wavelength: about 400 nm through 800 nm) of the retinal camera unit 1A, for example, a wavelength included in a range of about 800 nm through 900 nm.

The low-coherence light L0 emitted from the low-coherence light source 160 is guided to an optical coupler 162 through an optical fiber 161. The optical fiber 161 is composed of, for example, a single mode fiber or a PM (Polarization maintaining) fiber. The optical coupler 162 splits this low-coherence light L0 into a reference light LR and the signal light LS.

Although the optical coupler 162 acts as both a part (splitter) for splitting light and a part (coupler) for superposing lights, it will be herein referred to as an "optical coupler" idiomatically.

The reference light LR generated by the optical coupler 162 is guided by an optical fiber 163 composed of a single mode fiber or the like, and emitted from the end face of the fiber. The emitted reference light LR is converged into a parallel light flux by a collimator lens 171, passed through a glass block 172 and a density filter 173, and then reflected by a reference mirror 174 (reference object).

The reference light LR reflected by the reference mirror 174 is converged to the fiber end face of the optical fiber 163 by the collimator lens 171 again through the density filter 173 and the glass block 172. The converged reference light LR is guided to the optical coupler 162 through the optical fiber 163.

The glass block 172 and the density filter 173 act as a delaying part for making the optical path lengths (optical distances) of the reference light LR and the signal light LS coincide, and also as a dispersion correction part for making the dispersion characteristics of the reference light LR and the signal light LS coincide.

Further, the density filter 173 also acts as a dark filter for reducing the amount of the reference light, and is composed of a rotating ND (neutral density) filter, for example. This density filter 173 acts so as to change the reduction amount of the reference light LR by being rotary driven by a drive mechanism including a drive unit such as a motor (a density filter drive mechanism 244 described later; refer to FIG. 5). Consequently, it is possible to change the amount of the reference light LR contributing to generation of the interference-light LC.

Further, the reference mirror 174 is configured so as to move in the traveling direction (the direction of the arrow pointing both sides shown in FIG. 3) of the reference light LR. With this configuration, it is possible to ensure the optical path length of the reference light LR according to the axial length of the eye E, etc. Moreover, it is possible to capture an image of any depth position of the fundus oculi Ef, by moving the reference mirror 174. The reference mirror 174 is moved by a drive mechanism (a reference mirror driving mechanism 243 described later; refer to FIG. 5) including a driver such as a motor.

On the other hand, the signal light LS generated by the optical coupler 162 is guided to the end of the connection line 152 through an optical fiber 164 composed of a single mode fiber or the like. The conductive optical fiber 152a runs inside the connection line 152. Herein, the optical fiber 164 and the optical fiber 152a may be composed of a single optical fiber, or may be jointly formed by connecting the end faces of the respective fibers. In either case, it is sufficient as far as the optical fiber 164 and 152a are configured to be capable of transferring the signal light LS between the retinal camera unit 1A and the OCT unit 150.

The signal light LS is guided through the inside of the connection line 152 and led to the retinal camera unit 1A. Then, the signal light LS enters into the eye E through the lens 142, the scan unit 141, the dichroic mirror 134, the imaging lens 126, the relay lens 125, the variable magnifying lens 124, the imaging diaphragm 121, the aperture 112a of the aperture mirror 112, and the objective lens 113. The barrier filter 122 and 123 are retracted from the optical path in advance, respectively, when the signal light LS is made to enter the eye E.

The signal light LS having entered the eye E forms an image on the fundus oculi (retina) Ef and is then reflected. At this moment, the signal light LS is not only reflected on the surface of the fundus oculi Ef, but also scattered at the refractive index boundary after reaching the deep area of the fundus oculi Ef. As a result, the signal light LS passed through the fundus oculi Ef is a light containing information reflecting the state of the surface of the fundus oculi Ef and information reflecting the state of backscatter at the refractive index boundary of the deep area tissue of the fundus oculi Ef. This light may be simply referred to as "fundus oculi reflection light of the signal light LS."

The fundus oculi reflection light of the signal light LS travels reversely on the above path within the retinal camera unit 1A, and is converged at the end face 152b of the optical fiber 152a. Then, the signal light LS enters into the OCT unit 150 through the optical fiber 152a, and returns to the optical coupler 162 through the optical fiber 164.

The optical coupler 162 superimposes the signal light LS returning through the fundus oculi Ef and the reference light LR reflected by the reference mirror 174, thereby generating the interference-light LC. The generated interference-light LC is guided into a spectrometer 180 through an optical fiber 165 composed of a single mode fiber or the like.

Herein, although a Michelson-type interferometer is adopted in this embodiment, for instance, a Mach Zender type, etc. and any type of interferometer may be adopted appropriately. The "interference-light generator" related to the present invention comprises, for example, an optical coupler 162, an optical member on the optical path of the signal light LS (i.e., an optical member placed between the optical coupler 162 and the fundus oculi Ef), and an optical member on the optical path of the reference light LR (i.e., an optical member placed between the optical coupler 162 and the reference mirror 174), and specifically, comprises an interferometer equipped with the optical coupler 162, the optical fibers 163, 164, and the reference mirror 174.

The spectrometer 180 comprises a collimator lens 181, a diffraction grating 182, an image-forming lens 183, and a CCD 184. The diffraction grating 182 in this embodiment is a transmission-type diffraction grating that transmits light; however, needless to say, a reflection-type diffraction grating that reflects light may also be used. Moreover, needless to say, it is also possible to adopt, in place of the CCD 184, other photo-detecting elements.

The interference light LC having entered the spectrometer 180 is split (resolved into spectra) by the diffraction grating 182 after converged into a parallel light flux by the collimator lens 181. The split interference light LC forms an image on the image pick-up surface of the CCD 184 by the image-forming lens 183. The CCD 184 detects the respective spectra of the interference light LC and converts to electrical detection signals, and outputs the detection signals to the arithmetic control unit 200. The CCD 184 functions as the "detector" of the present invention.

Configuration of Arithmetic Control Unit

Next, the configuration of the arithmetic control unit 200 will be described. The arithmetic control unit 200 performs a process of analyzing detection signals inputted from the CCD 184 of the spectrometer 180 of the OCT unit 150 and forming a tomographic image of the fundus oculi Ef of the eye E. The analysis method is the same as the conventional technique of Fourier Domain OCT.

Further, the arithmetic control unit 200 performs a process of forming (image data of) a 2-dimensional image showing the state of the surface (retina) of the fundus oculi Ef, based on the video signals outputted from the imaging devices 10 and 12 of the retinal camera unit 1A.

Furthermore, the arithmetic control unit 200 executes control of each part of the retinal camera unit 1A and the OCT unit 150.

The arithmetic control unit 200 executes as control of the retinal camera unit 1A, for example: control of emission of illumination light by the observation light source 101 or the imaging light source 103; control of insertion/retraction operations of the exciter filters 105 and 106 or the barrier filters 122 and 123 to/from the optical path; control of the operation of a display device such as the LCD 140; control of shift of the illumination diaphragm 110 (control of the diaphragm value); control of the diaphragm value of the imaging diaphragm 121; and control of shift of the variable magnifying lens 124 (control of the magnification). Moreover, the arithmetic control unit 200 executes control of the operation of the Galvano mirrors 141A and 141B inside the scan unit 141 (operation of changing the directions of the reflection faces).

Further, the arithmetic control unit 200 executes as control of the OCT unit 150, for example: control of emission of the low-coherence light L0 by the low-coherence light source 160; control of shift of the reference mirror 174; control of the rotary operation of the density filter 173 (operation of changing the reduction amount of the reference light LR); and control of the accumulated time of the CCD 184.

One example of the hardware configuration of the arithmetic and control unit 200 that acts as described above will be described referring to FIG. 4.

The arithmetic and control unit 200 is provided with the same hardware configuration as that of a conventional computer. To be specific, the arithmetic and control unit 200 comprises: a microprocessor 201 (CPU, MPU, etc.), a RAM 202, a ROM 203, a hard disk drive (HDD) 204, a keyboard 205, a mouse 206, a display 207, an image forming board 208, and a communication interface (I/F) 209. These parts are connected via a bus 200a.

The microprocessor 201 comprises a CPU (Central Processing Unit), an MPU (Micro Processing Unit) or the like, and executes operations characteristic to this embodiment, by loading a control program 204a stored in the hard disk drive 204, onto the RAM 202. Further, the microprocessor 201 executes control of each part of the device described above, various arithmetic processes, etc. Moreover, the microprocessor 201 executes control of each part of the device corresponding to an operation signal from the keyboard 205 or the mouse 206, control of a display process by the display 207, and control of a transmission/reception process of various data, control signals and so on by the communication interface 209.

The keyboard 205, the mouse 206 and the display 207 are used as user interfaces in the fundus oculi observation device 1. The keyboard 205 is used as, for example, a device for typing letters, figures, etc. The mouse 206 is used as a device for performing various input operations to the display screen of the display 207.

Further, the display 207 is any display device composed of an LCD, a CRT (Cathode Ray Tube) display or the like. The display 207 displays various images of the fundus oculi Ef formed by the fundus oculi observation device 1, and displays various screens such as an operation screen and a set-up screen.

The user interface of the fundus oculi observation device 1 is not limited to the above configuration, and may be configured by using any user interface having a function of displaying and outputting various information, and a function of inputting various information and operating the device, such as a track ball, a control lever, a touch panel type of LCD, and a control panel for ophthalmology examinations.

The image forming board 208 is a dedicated electronic circuit for a process of forming (image data of) images of the fundus oculi Ef of the eye E. This image forming board 208 is provided with a fundus oculi image forming board 208a and an OCT-image forming board 208b.

The fundus oculi image forming board 208a is a dedicated electronic circuit that operates to form image data of fundus oculi images based on the video signals from the imaging device 10 and the imaging device 12 of the retinal camera unit 1A.

Further, the OCT-image forming board 208b is a dedicated electronic circuit that operates to form image data of tomographic images of the fundus oculi Ef, based on the detection signals from the CCD 184 of the spectrometer 180 in the OCT unit 150.

By providing the image forming board 208, it is possible to increase the processing speed for forming image data of fundus oculi images and tomographic images.

The communication interface 209 performs a process of sending control signals from the microprocessor 201, to the retinal camera unit 1A or the OCT unit 150. Moreover, the communication interface 209 performs a process of receiving video signals from the imaging devices 10 and 12 of the retinal camera unit 1A and detection signals from the CCD 184 of the OCT unit 150, and inputting the signals to the image forming board 208. At this time, the communication interface 209 operates to input the video signals from the imaging devices 10 and 12, to the fundus oculi image forming board 208a, and input the detection signal from the CCD 184, to the OCT-image forming board 208b.

Further, in a case where the arithmetic and control unit 200 is connected to a network such as a LAN (Local Area Network) and the Internet, it is possible to configure so as to be capable of data communication via the network, by providing the communication interface 209 with a network adapter like a LAN card or communication equipment like a modem. In this case, by mounting a server accommodating the control program 204a on the network, and at the same time, configuring the arithmetic and control unit 200 as a client terminal of the server, it is possible to cause the fundus oculi observation device 1 to execute the operation according to the present invention.

Configuration of Control System

Next, the configuration of the control system of the fundus oculi observation device 1 will be described referring to FIG. 5 through FIG. 7. FIG. 5 is a block diagram showing a part related to the operations and processes according to the present invention particularly selected from among constituents composing the fundus oculi observation device 1. FIG. 6 shows one example of the configuration of the operation panel 3a disposed to the retinal camera unit 1A. FIG. 7 is a block diagram showing a detailed configuration of the arithmetic and control unit 200.

(Controller)

The control system of the fundus oculi observation device 1 is configured mainly having a controller 210 of the arithmetic and control unit 200 shown in FIG. 5. The controller 210 comprises the microprocessor 201, the RAM202, the ROM203, the hard disk drive 204 (control program 204a), and the communication interface 209.

The controller 210 executes the aforementioned controlling processes through the microprocessor 201 operating based on the control program 204a. In specific, for the retinal camera unit 1A, the controller 210 performs control of the mirror drive mechanisms 241 and 242 for changing the positions of the Galvano mirrors 141A and 141B, control of the display operation of the internal fixation target by the LCD 140, etc.

Further, for the OCT unit 150, the controller 210 performs control of the low-coherence light source 160 and the CCD 184, control of the density filter drive mechanism 244 for rotating the density filter 173, control of the reference-mirror driving mechanism 243 for moving the reference mirror 174 in the traveling direction of the reference light LR, etc.

Herein, the reference-mirror driving mechanism 243 functions as one example of the "driver" of the present invention. Moreover, the controller 210 functions as one example of the "controller" of the present invention.

Furthermore, the controller 210 performs control for causing the display 240A of the user interface (UI) 240 to display two kinds of images photographed by the fundus oculi observation device 1: that is, a 2-dimensional image of the surface of the fundus oculi Ef obtained by the retinal camera unit 1A, and a tomographic image of the fundus oculi Ef formed based on the detection signals obtained by the OCT unit 150. These images may be displayed on the display 240A separately, or may be displayed side by side simultaneously.

(Movement-Distance Determining Part)

The controller 210 comprises a movement-distance determining part 211. The movement-distance determining part 211 compares the result of calculation of a movement distance of the reference mirror 174 with an actual movement distance, which will be described in detail later.

(Image Forming Part)

An image forming part 220 performs a process of forming image data of the fundus oculi image based on the video signals from the imaging devices 10 and 12 of the retinal camera unit 1A, and a process of forming image data of the tomographic images of the fundus oculi Ef based on the detection signals from the CCD 184 of the OCT unit 150.

In particular, in the image-forming process based on the detection signals from the OCT unit 150, the image forming part 220 forms a tomographic image within a predetermined frame. Herein, the frame refers to a frame that becomes the range of formation of an image. At the time of displaying an image, an image formed within the frame is to be displayed.

When the retinal camera unit 1A is moved in the x-direction or y-direction, an image formed within the frame changes in the surface direction of the fundus oculi Ef. Furthermore, when the reference mirror 174 is moved, namely, when the optical path length of the reference light LR is changed, the depth position of an image formed within the frame changes. Thus, by appropriately aligning the position of the retinal camera unit 1A or the position of the reference mirror 174, it is possible to form an image of the fundus oculi Ef at a desired position and depth within the frame.

The imaging forming part 220 comprises the imaging forming board 208 and the communication interface 209. In this specification, "image" may be identified with "image data" corresponding thereto. Herein, the image forming part 220 (OCT-image forming board 208b) functions as one example of the "image forming part" of the present invention.

(Image Processor)

The image processor 230 applies various image processing and analysis process to image data of images formed by the image forming part 220. For example, the image processor 230 executes a process of forming image data of a 3-dimensional image of the fundus oculi Ef based on the tomographic images corresponding to the detection signal from the OCT unit 150, and various correction processes such as brightness correction and dispersion correction of the images.

Herein, image data of a 3-dimensional image is image data made by assigning pixel values to each of a plurality of voxels arranged 3-dimensionally, and is referred to as volume data, voxel data, and the like. When displaying an image based on volume data, the image processor 230 operates to apply a rendering process (such as volume rendering and MIP (Maximum Intensity Projection)) to this volume data and form image data of a pseudo 3-dimensional image seen from a specified viewing direction. On a display device such as the display 207, the pseudo 3-dimensional image based on the image data is displayed.

Furthermore, an analyzing part 231 is disposed to the image processor 230. The analyzing part 231 conducts analytical processes for alignment of a measurement position in the depth direction of the fundus oculi Ef and functions as an example of the "analyzer" in the present invention. The analyzing part 231 includes a signal-level calculator 232, a signal-level determining part 233, an image-position specifying part 234, and a movement-distance calculator 235. Hereinafter, each of these parts 232 through 235 will be described.

(Signal-Level Calculator)

The signal-level calculator 232 analyzes an image (OCT image) formed by the OCT-image forming board 208b of the image forming part 220 and calculates the signal level of the OCT image. As for the method of calculating the signal level of the image, it is possible to use any known method. The OCT image to become the subject for calculation of the signal level may be a 2-dimensional tomographic image, or may be a 1-dimensional image of the depth direction (to be described later). Herein, the signal level refers to the intensity of signal components included in the image data of an OCT image, and is the intensity of a component obtained after (at least part of) a noise component is removed from the image data of the OCT image. This signal component is a component in which morphology of the fundus oculi Ef has been reflected.

(Signal-Level Determining Part)

The signal-level determining part 233 determines the size relation by comparing the signal level value calculated by the signal-level calculator 232 with a predetermined threshold value. The threshold value is previously set and stored in a hard disk drive 204a or the like.

(Image-Position Specifying Part)

The image-position specifying part 234 analyzes the OCT image whose signal level is determined to be over the threshold value by the signal-level determining part 233, and finds the position of the predetermined partial image in the frame previously described. This partial image is, for example, an image corresponding to a predetermined depth position of the fundus oculi Ef. As the depth position, for example, of a plurality of layers composing the fundus oculi Ef (nerve fiber layer, photoreceptor layer, retinal pigment epithelium, etc.), a layer in which the pixel value (brightness value or the like) within the OCT image becomes the greatest.

The partial image specified by the image-position specifying part 234 is not limited to those described above but may also be an image equivalent to any layer among the plurality of layers composing the fundus oculi Ef. Moreover, it is possible to specify an image region equivalent to the surface of the fundus oculi Ef as the partial region described above (Movement-Distance Calculator)

The movement-distance calculator 235 calculates the distance of movement of the reference mirror 174 based on the position of the partial image specified by the image-position specifying part 234.

To explain more concretely, first, the movement-distance calculator 235 calculates the displacement between the position of a partial image within the frame obtained by the image-position specifying part 234 and a specific position within the frame. This specific position is previously set as the predetermined depth position within the frame. Furthermore, this specific position is set at a position within a frame where the measurement sensitivity in measurement for capturing an OCT image is relatively favorable.

Assuming a coordinate value of the depth direction (z-direction) of the specific position within the frame is z0 and a coordinate value of the specified position of the partial image is z, the movement-distance calculator 235 calculates displacement $\Delta z = z - z0$. This method is effective, for example, when the partial image is a 1-dimensional image or when the z coordinate values of the respective pixels composing a 2-dimensional partial image are the same.

On one hand, in a case in which the partial image is a 2-dimensional image and also includes a pixel of different z coordinate value, it is difficult to employ the above method. Moreover, in a case in which the partial image includes a plurality of 1-dimensional images, it is also difficult to employ the above method. Then, in these cases, for example, the displacement $\Delta z$ can be found by employing a method as follows.

First, a z coordinate value z1 of a specified pixel of the specified partial image is found, and this z coordinate value z1 is assumed to be a z coordinate value of the partial image. Then, z1−z0 is calculated, and the result of this calculation is assumed to be the displacement $\Delta z$. Herein, as the above-described specified pixel, for example, a pixel with the maximum or minimum z coordinate value, a pixel with a medium z coordinate value (in the middle of the maximum and the minimum), and a pixel that becomes a center in a direction orthogonal to a depth direction may be used.

Another method may be to define the average value of the z coordinate values of a plurality of pixels composing a partial image as a z coordinate value of the partial image. For example, in a case in which a partial image composed of a plurality of 1-dimensional images (images of the depth direction to be described later) is taken into consideration, a pixel with the maximum pixel value is specified in each of the 1-dimensional images, and the average value of the z coordinate values of the specified plurality of pixels can be defined as a z coordinate value of the partial image.

After the displacement $\Delta z$ is calculated as described above, the movement-distance calculator 235 calculates the movement distance of the reference mirror 174 corresponding to this displacement $\Delta z$. The distance of z-direction within a frame is previously associated with the distance of the depth direction (z-direction) of the fundus oculi Ef. The movement-distance calculator 235 calculates the distance of the depth direction of the fundus oculi Ef that corresponds to the displacement $\Delta z$ within the frame, based on the association of the distances. In an optical image measurement device, an image of the fundus oculi Ef is captured at the almost the same depth position as the optical distance from the optical coupler 162 to the reference mirror 174. Therefore, the movement distance of the reference mirror 174 becomes equal to the distance of the depth direction of the fundus oculi Ef calculated by the movement-distance calculator 235.

The image processor 230 that operates as described above comprises the microprocessor 201, the RAM 202, the ROM 203, and the hard disk drive 204 (control program 204a).

(User Interface)

The user interface (UI) 240 comprises the display 240A and an operation part 240B. The display 240A is composed of a display device such as the display 207. Further, the operation part 240B is composed of an input device or an operation device such as the keyboard 205 and the mouse 206.

(Operation Panel)

The operation panel 3a of the retinal camera unit 1A will be described. The operation panel 3a is arranged on the platform (not shown) of the retinal camera unit 1A, for example.

The operation panel 3a is provided with an operating part used to instruct an operation for capturing a 2-dimensional image of the surface of the fundus oculi Ef, and an operating part used to instruct an operation for capturing a tomographic image of the fundus oculi Ef.

Placement of the operation panel 3a makes it possible to execute an operation for capturing a fundus oculi image Ef' and an operation for capturing a tomographic image in the same manner as when operating a conventional retinal camera.

As shown in FIG. 6, the operation panel 3a is provided with, for example, a menu switch 301, a split switch 302, an imaging light amount switch 303, an observation light amount switch 304, a jaw holder switch 305, a photographing switch 306, a zoom switch 307, an image switching switch 308, a fixation target switching switch 309, a fixation target position adjusting switch 310, a fixation target size switching switch 311, and a mode switching knob 312.

The menu switch 301 is a switch operated to display a certain menu screen for a user to select and designate various menus (such as an imaging menu for imaging a 2-dimensional image of the surface of the fundus oculi Ef, a tomographic image and the like, and a setting menu for inputting various settings).

When this menu switch 301 is operated, the operation signal is inputted to the controller 210. The controller 210 causes the touch panel monitor 11 or the display 240A to display a menu screen, in response to the input of the operation signal. A controller (not shown) may be provided in the retinal camera unit 1A, whereby the controller causes the touch panel monitor 11 to display the menu screen.

The split switch 302 is a switch operated to switch the light on and off of the split bright line for focusing (e.g., see Japanese Unexamined Patent Application Publication JP-A 9-66031. Also referred to as split target, split mark and so on.). The configuration for projecting this split bright line onto the eye E (split bright line projection part) is housed, for example, in the retinal camera unit 1A (not shown in FIG. 1).

When this split switch 302 is operated, the operation signal is inputted to the controller 210 (or the aforementioned controller inside the retinal camera unit 1A; the same hereinafter). The controller 210 projects the split bright line onto the eye E by controlling the split bright line projection part, in response to the input of this operation signal.

The imaging light amount switch 303 is a switch operated to adjust the emitted light amount of the imaging light source 103 (photographing light amount) depending on the state of the eye E (such as the degree of opacity of the lens). This imaging light amount switch 303 is provided with, for example, a photographing light amount increasing switch "+" for increasing the photographing light amount, a photographing light amount decreasing switch "−" for decreasing the photographing light amount, and a reset switch (a button in the middle) for setting the photographing light amount to a predetermined initial value (default value).

When one of the imaging light amount switches 303 is operated, the operation signal is inputted to the controller 210. The controller 210 controls the imaging light source 103 in response to the inputted operation signal and adjusts the photographing light amount.

The observation light amount switch 304 is a switch operated to adjust the emitted light amount (observation light amount) of the observation light source 101. The observation light amount switch 304 is provided with, for example, an observation light amount increasing switch "+" for increasing the observation light amount, and an observation light amount decreasing switch "−" for decreasing the observation light amount.

When one of the observation light amount switches 304 is operated, the operation signal is inputted to the controller 210. The controller 210 controls the observation light source 101 in response to the inputted operation signal and adjusts the observation light amount.

The jaw holder switch 305 is a switch to move the position of the jaw holder (not shown) of the retinal camera unit 1A. This jaw holder switch 305 is provided with, for example, an upward movement switch (upward triangle) for moving the jaw holder upward, and a downward movement switch (downward triangle) for moving the jaw holder downward.

When one of the jaw holder switches 305 is operated, the operation signal is inputted to the controller 210. The controller 210 controls a jaw holder movement mechanism (not shown) in response to the inputted operation signal and moves the jaw holder upward or downward.

The photographing switch 306 is a switch used as a trigger switch for capturing a 2-dimensional image of the surface of the fundus oculi Ef or a tomographic image of the fundus oculi Ef.

When the photographing switch 306 is operated in a state where a menu to photograph a 2-dimensional image is selected, the controller 210 that has received the operation signal controls the imaging light source 103 to emit photographing illumination light, and also causes the display 240A or the touch panel monitor 11 to display a 2-dimensional image of the surface of the fundus oculi Ef, based on the video signal outputted from the imaging device 10 having detected the fundus oculi reflection light.

On the other hand, when the photographing switch 306 is operated in a state where a menu to capture a tomographic image is selected, the controller 210 that has received the operation signal controls the low-coherence light source 160 to emit the low-coherence light L0, and also controls the Galvano mirrors 141A and 141B to scan the signal light LS. Moreover, the controller 210 causes the display 240A or the touch panel monitor 11 to display a tomographic image of the fundus oculi Ef formed by the image forming part 220 (and image processor 230), based on the detection signal outputted from the CCD 184 that has detected the interference light LC.

The zoom switch 307 is a switch operated to change the angle of view (zoom magnification) at the time of photographing of the fundus oculi Ef. Every time this zoom switch 307 is operated, the photographing angle is set alternately to 45 degrees and 22.5 degrees, for example.

When this zoom switch 307 is operated, the controller 210 that has received the operation signal controls a variable magnifying lens driving mechanism (not shown) to move the variable magnifying lens 124 in the optical axis direction of the imaging optical system 120, thereby changing the photographing angle of view.

The image switching switch 308 is a switch operated to switch displayed images. When the image switching switch 308 is operated in a state where a fundus oculi observation image (a 2-dimensional image of the surface of the fundus oculi Ef based on the video signal from the imaging device 12) is displayed on the display 240A or the touch panel monitor 11, the controller 210 having received the operation signal controls the display 240A or touch panel monitor 11 to display the tomographic image of the fundus oculi Ef.

On the other hand, when the image-switching switch 308 is operated in a state where a tomographic image of the fundus oculi is displayed on the display 240A or the touch pane monitor 11, the controller 210 having received the operation signal controls the display 240A or the touch panel monitor 11 to display the fundus oculi observation image.

The fixation target-switching switch 309 is a switch operated to switch the position of the internal fixation target displayed by the LCD 140 (i.e. the projection position of the internal fixation target on the fundus oculi Ef). By operating this fixation target switching switch 309, the display position of the internal fixation target can be switched, for example, among "fixation position to capture the image of the peripheral region of the center of the fundus oculi (fixation position for fundus oculi center imaging)," "fixation position to capture the image of the peripheral region of macula lutea (fixation position for macula lutea imaging)" and "fixation position to capture the image of the peripheral region of papilla (fixation position for papilla imaging)," in a circulative fashion.

In response to the operation signals from the fixation target-switching switch 309, the controller 210 causes the LCD 140 to display the internal fixation target in different positions on the display surface thereof. The display positions of the internal fixation target corresponding to the above three fixation positions, for example, can be preset based on clinical data, or can be set for each eye or for each image photographing in advance.

The fixation target position-adjusting switch 310 is a switch operated to adjust the display position of the internal fixation target. This fixation target position adjusting switch 310 is provided with, for example, an upward movement switch for moving the display position of the internal fixation target upward, a downward movement switch for moving it downward, a leftward movement switch for moving it leftward, a rightward movement switch for moving it rightward, and a reset switch for moving it to a predetermined initial position (default position).

Upon reception of the operation signal from either of these switches of the fixation target position-adjusting switch 310, the controller 210 controls the LCD 140 to move the display position of the internal fixation target, in response to the operation signal.

The fixation target size switching switch 311 is a switch operated to change the size of the internal fixation target. When this fixation target size switching switch 311 is operated, the controller 210 that has received the operation signal controls the LCD 140 to change the display size of the internal fixation target. The display size of the internal fixation target can be switched, for example, between "normal size" and "enlarged size," alternately. As a result, the size of the projection image of the fixation target projected onto the fundus oculi Ef is changed. Upon reception of the operation signal from the fixation target position adjusting switch 311, the controller 210 controls the LCD 140 to change the display size of the internal fixation target, in response to the operation signal.

The mode-switching knob 312 is a knob rotationally operated to select various photographing modes. The photographing modes are, for example, a fundus oculi photographing mode to photograph a 2-dimensional image of the fundus oculi Ef, a B-scan mode to perform B-scan of the signal light LS, and a 3-dimensional scan mode to scan with the signal light LS 3-dimensionally. In addition, the mode-switching knob 312 may be configured so as to be capable of selecting a replay mode to replay and display a captured 2-dimensional image or tomographic image of the fundus oculi Ef. In addition, it may be configured so as to be capable of selecting a photographing mode to control so that the photographing of the fundus oculi Ef would be performed immediately after scanning of the signal light LS. Control of each part of the device for causing the fundus oculi observation device 1 to execute the operation corresponding to the each mode is executed by the controller 210.

Herein, the feature of control of scanning of the signal light LS by the controller 210, and the feature of processing to the detection signal from the OCT unit 150 by the image forming part 220 and the image processor 230 will be respectively described. An explanation regarding the process by the image forming part 220, etc., to the video signal from the retinal camera unit 1A will be omitted because it is the same as the conventional process.

Signal Light Scanning

Scanning of the signal light LS is performed by changing the positions (directions of the reflecting surfaces) of the Galvano mirrors 141A and 141B of the scan unit 141 in the retinal camera unit 1A. By controlling the mirror drive mechanisms 241 and 242 respectively to change the directions of the reflecting surfaces of the Galvano mirrors 141A and 141B respectively, the controller 210 scans the application position of the signal light LS on the fundus oculi Ef.

When the facing direction of the reflecting surface of the Galvano mirror 141A is changed, the signal light LS is scanned in the horizontal direction (x-direction in FIG. 1) on the fundus oculi Ef. Whereas, when the facing direction of the reflecting surface of the Galvano mirror 141B is changed, the signal light LS is scanned in the vertical direction (y-direction in FIG. 1) on the fundus oculi Ef. Further, by changing the facing directions of the reflecting surfaces of both the Galvano mirrors 141A and 141B simultaneously, it is possible to scan the signal light LS in the composed direction of the x-direction and y-direction. That is, by controlling these two Galvano mirrors 141A and 141B, it is possible to scan the signal light LS in any direction on the x-y plane.

Figure 8A:
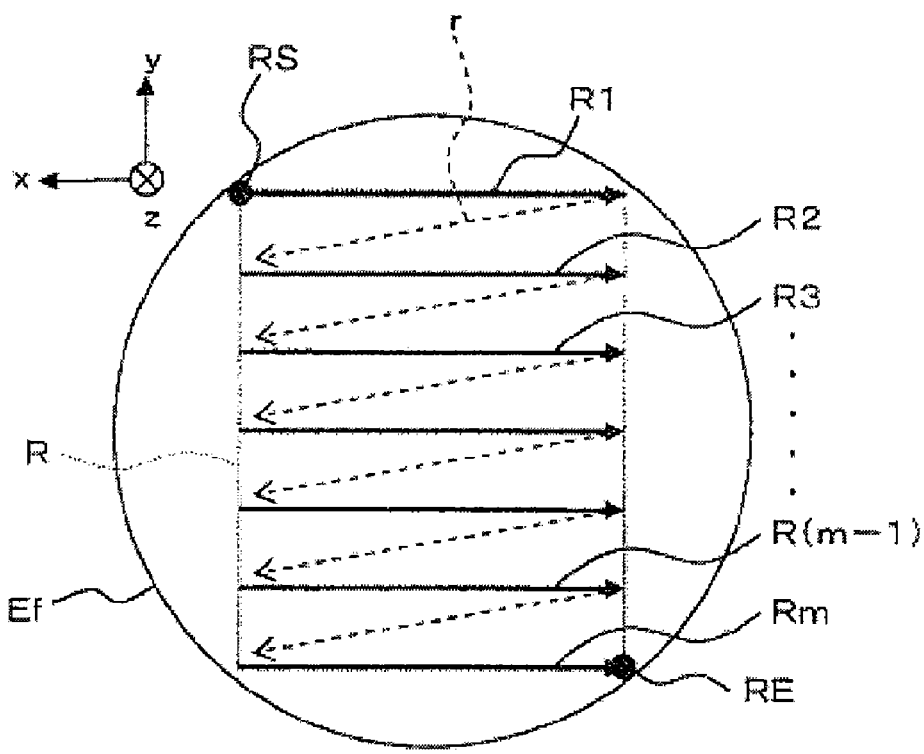
FIGS. 8A and 8B are schematic views showing one example of a scanning pattern of a signal light in the preferred embodiment of the device related to the present invention.
Figure 8B:
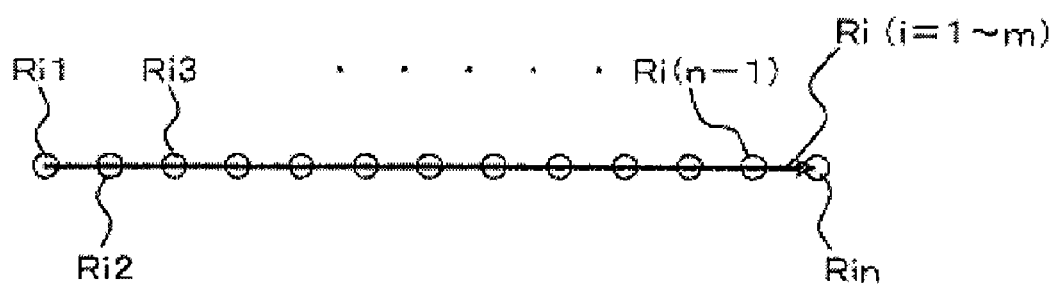

FIGS. 8A and 8B shows one example of the feature of scanning of the signal light LS for forming images of the fundus oculi Ef. FIG. 8A shows one example of the feature of scanning of the signal light LS, when the fundus oculi Ef is seen from a direction that the signal light LS enters the eye E (that is, seen from −z side toward +z side in FIG. 1). Further, FIG. 8B shows one example of the feature of arrangement of scanning points (positions at which image measurement is carried out; target positions of the signal light LS) on each scanning line on the fundus oculi Ef.

As shown in FIG. 8A, the signal light LS is scanned within a rectangular-shaped scanning region R that has been preset. Within this scanning region R, a plurality of (m number of) scanning lines R1 through Rm are set in the x-direction. When the signal light LS is scanned along the respective scanning lines Ri (i=1 through m), detection signals of the interference light LC are generated.

Herein, a direction of each scanning line Ri will be referred to as the "main scanning direction" and a direction orthogonal thereto will be referred to as the "sub-scanning direction". Accordingly, scanning of the signal light LS in the main scanning direction is performed by changing the facing direction of the reflecting surface of the Galvano mirror 141A, and scanning in the sub-scanning direction is performed by changing the facing direction of the reflecting surface of the Galvano mirror 141B.

On each scanning line Ri, as shown in FIG. 8B, a plurality of (n number of) scanning points Ri1 through Rin are preset.

In order to execute the scanning shown in FIGS. 8A and 8B, the controller 210 firstly controls the Galvano mirrors 141A and 141B to set the target of the signal light LS entering into the fundus oculi Ef to a scan start position RS (scanning point R11) on the first scanning line R1. Subsequently, the controller 210 controls the low-coherence light source 160 to flush the low-coherence light L0, thereby making the signal light LS enter the scan start position RS. The CCD 184 receives the interference light LC based on the fundus oculi reflection light of this signal light LS at the scan start position RS, and outputs the detection signal to the controller 210.

Next, the controller 210 controls the Galvano mirror 141A to scan the signal light LS in the main scanning direction and set the incident target of the signal light LS to a scanning point R12, and makes the low-coherence light L0 flushed to make the signal light LS enter into the scanning point R12. The CCD 184 receives the interference light LC based on the fundus oculi reflection light of this signal light LS at the scanning point R12, and then outputs the detection signal to the controller 210.

Likewise, the controller 210 obtains detection signals outputted from the CCD 184 in response to the interference light LC for each scanning point, by flushing the low-coherence light L0 at each scanning point while shifting the incident target of the signal light LS from scanning point R13 to R14, —, R1 (n-1), and R1n in order.

Once the measurement at the last scanning point R1n of the first scanning line R1 is finished, the controller 210 controls the Galvano mirrors 141A and 141B simultaneously to shift the incident target of the signal light LS to the first scanning point R21 of the second scanning line R2 following a line switching scan r. Then, by conducting the previously described measurement on each scanning point R2j (j=1 through n) of this second scanning line R2, detection signals corresponding to the respective scanning points R2j are obtained.

Likewise, the measurement is conducted for each of the third scanning line R3, —, the m-1th scanning line R(m-1), the mth scanning line Rm to obtain the detection signals corresponding to the respective scanning points. Symbol RE on a scanning line Rm is a scan end position corresponding to a scanning point Rmn.

As a result, the controller 210 obtains m×n number of detection signals corresponding to m×n number of scanning points Rij (i=1 through m, j=1 through n) within the scanning region R. Hereinafter, a detection signal corresponding to the scanning point Rij may be represented by Dij.

Such interlocking control of the shift of scanning points and the emission of the low-coherence light L0 can be realized by synchronizing, for instance, timing for transmission of control signals to the mirror drive mechanisms 241 and 242 and timing for transmission of control signals (output request signals) to the low-coherence light source 160.

As described above, when each of the Galvano mirrors 141A and 141B is operated, the controller 210 stores the position of each scanning line Ri and the position of each scanning point Rij (coordinates on the x-y coordinate system) as information representing the content of the operation. This stored content (scanning point coordinate information) is used in an image forming process as in conventional one.

Image Processing

Next, one example of a process on OCT images (tomography images of the fundus oculi Ef) by the image forming part 220 and the image processor 230 will be described.

The image forming part 220 executes the formation process of tomographic images of the fundus oculi Ef along each scanning line Ri (main scanning direction). Further, the image processor 230 executes the formation process of a 3-dimensional image of the fundus oculi Ef based on these tomographic images formed by the image forming part 220, etc.

The formation process of a tomographic image by the image forming part 220, as in the conventionally one, includes a 2-step arithmetic process. In the first step of the arithmetic process, based on a detection signal Dij corresponding to each scanning point Rij, an image in the depth-wise direction (z-direction in FIG. 1) of the fundus oculi Ef at the scanning point Rij is formed.

Figure 9:
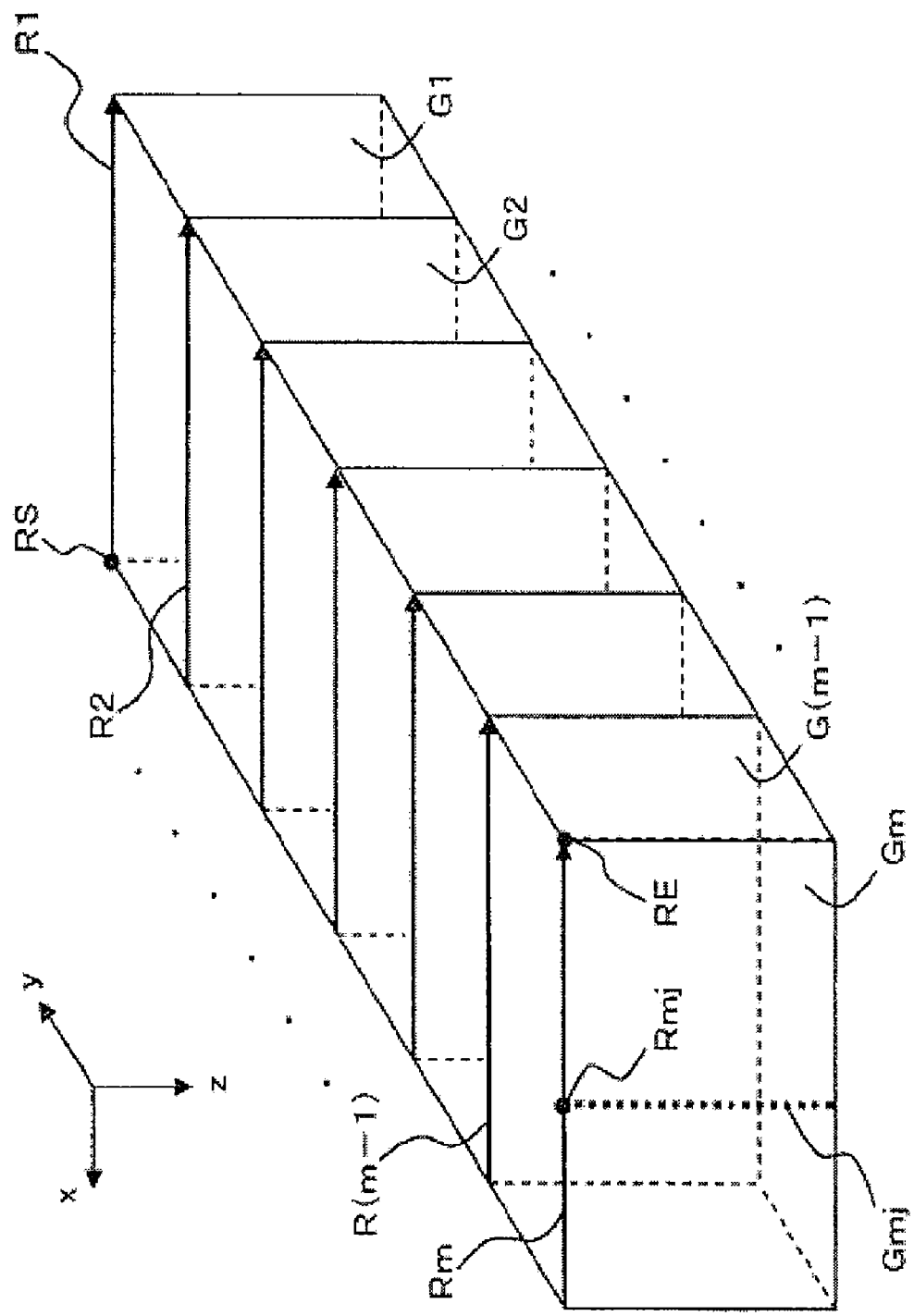
FIG. 9 is a schematic view showing one example of a scanning pattern of the signal light and a pattern of a tomographic image formed along each scanning line in the preferred embodiment of the device related to the present invention.

FIG. 9 shows a feature of (a group of) tomographic images formed by the image forming part 220. In the second step of the arithmetic process, on each scanning line Ri, based on the images in the depth-wise direction at the n number of scanning points Ri1 through Rin, a tomographic image Gi of the fundus oculi Ef along the scanning line Ri is formed. Then, the image forming part 220 determines the arrangement and the distance of the scanning points Ri1 through Rin referring to the positional information (scanning point coordinate information described before) of the scanning points Ri1 through Rin, and forms a tomographic image Gi along this scanning line Ri.

Through the above process, m number of tomographic images (a group of tomographic images) G1 through Gm at different positions in the sub-scanning direction (y-direction) are obtained.

Next, the formation process of a 3-dimensional image of the fundus oculi Ef by the image processor 230 will be explained. A 3-dimensional image of the fundus oculi Ef is formed based on the m number of tomographic images obtained through the above arithmetic process. The image processor 230 forms a 3-dimensional image of the fundus oculi Ef by performing a known interpolating process to interpolate an image between the adjacent tomographic images Gi and G(i+1).

Here, the formation process of a 3-dimensional image of the fundus oculi Ef by the image processor 230 will be explained. A 3-dimensional image of the fundus oculi Ef is formed based on the m number of tomographic images obtained through the above arithmetic process. The image processor 230 forms a 3-dimensional image of the fundus oculi Ef by performing a known interpolating process to interpolate an image between the adjacent tomographic images Gi and G(i+1).

Furthermore, based on this 3-dimensional image, the image processor 230 can form a tomographic image of the fundus oculi Ef at a cross-section in any direction other than the main scanning direction (x-direction). Once the cross-section is designated, the image processor 230 determines the position of each scanning point (and/or an interpolated depth-wise image) on this designated cross-section, and extracts a depth-wise image at each determined position (and/or an interpolated depth-wise image), thereby forming a tomographic image of the fundus oculi Ef at the designated cross-section by arranging plural extracted depth-wise images.

Furthermore, an image Gmj shown in FIG. 9 represents an image in the depth-wise direction (z-direction) at the scanning point Rmj on the scanning line Rm. A depth-wise image at each scanning point Rij on the scanning line Ri formed by the first-step arithmetic process is represented as "image Gij."

[Usage Pattern]

Figure 10:
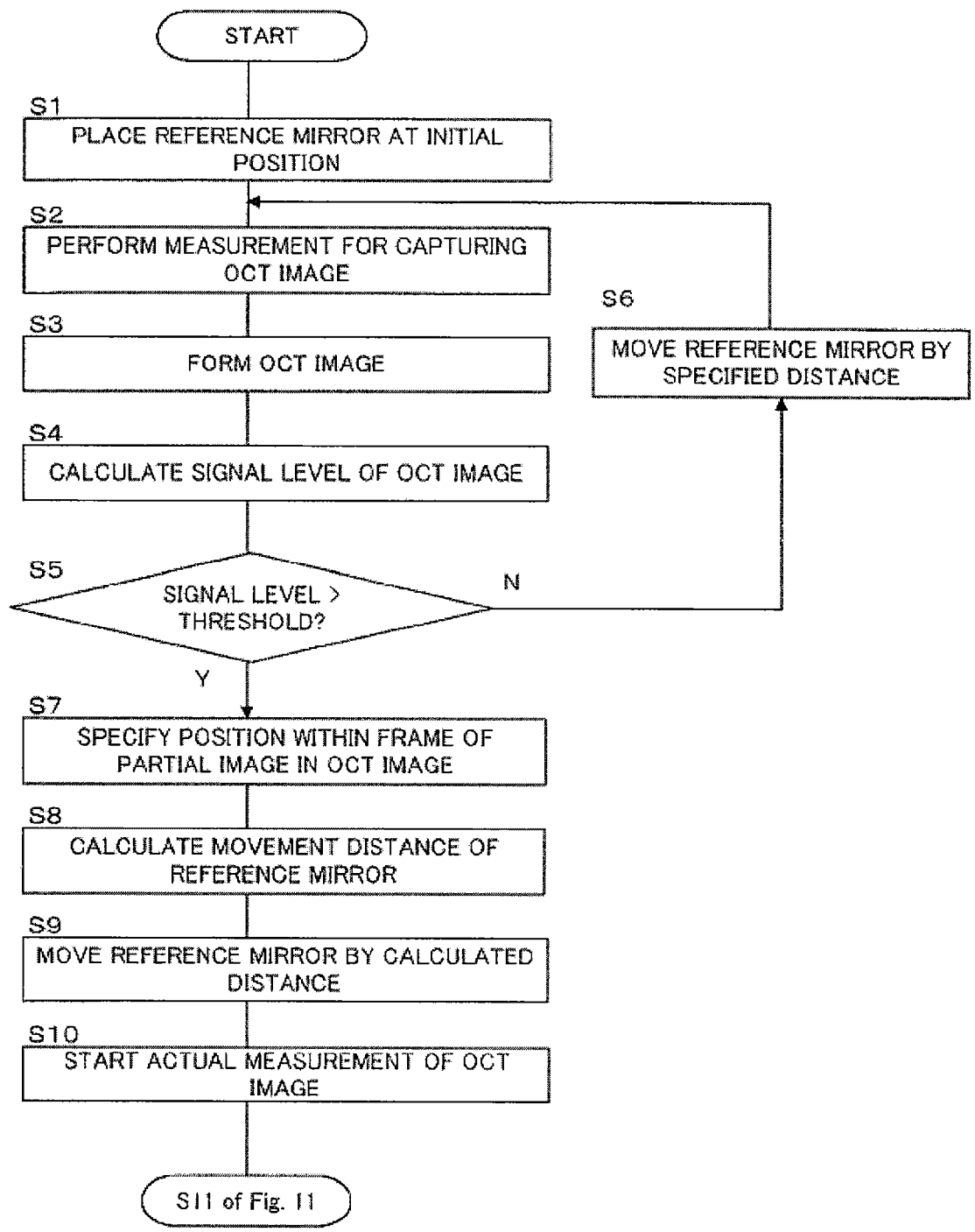
FIG. 10 is a flowchart showing one example of a usage pattern in the preferred embodiment of the device related to the present invention.
Figure 11:
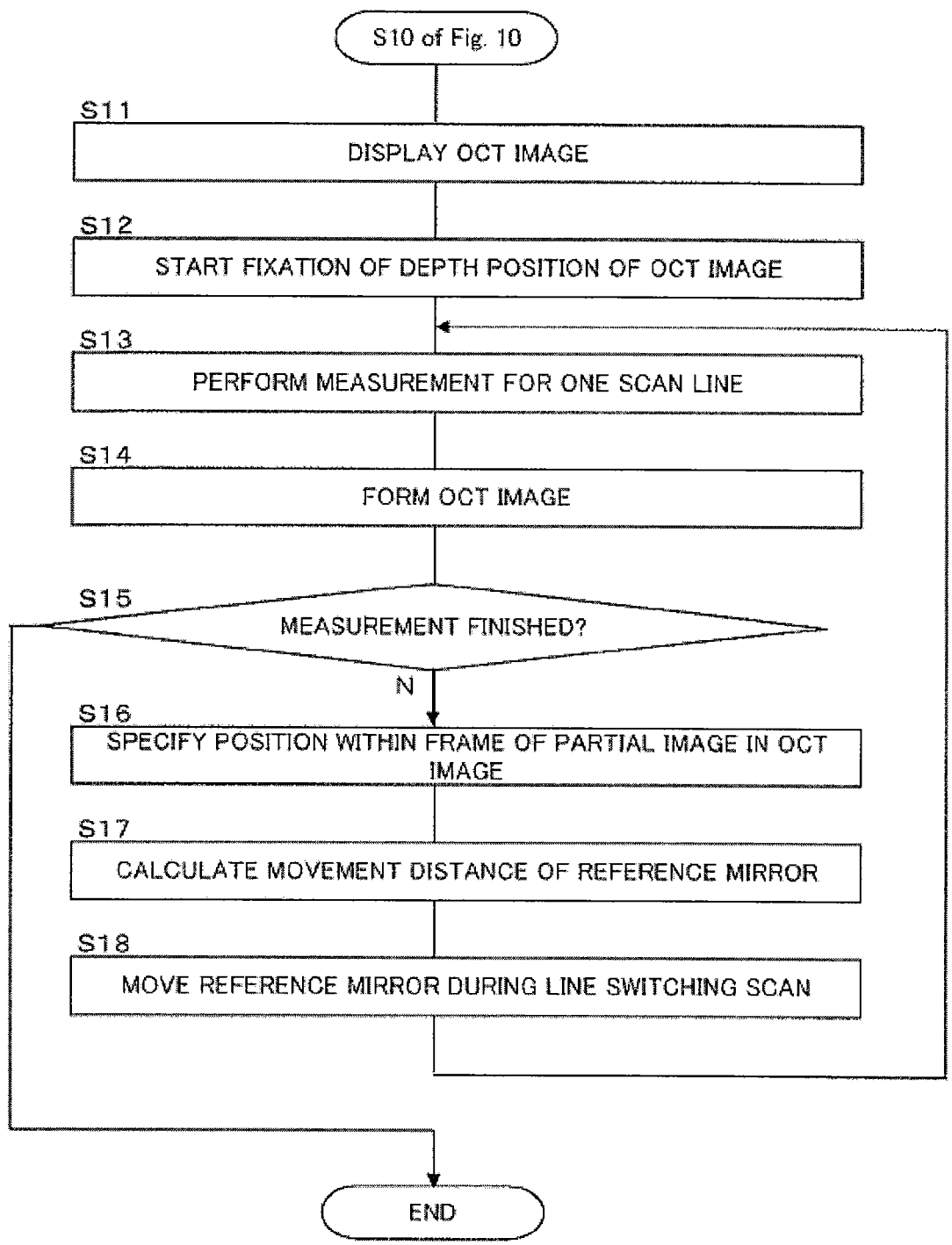
FIG. 11 is a flowchart showing one example of a usage pattern in the preferred embodiment of the device related to the present invention.

A usage pattern of the fundus oculi observation device 1 having the configuration as described above will be explained. Flowcharts shown in FIGS. 10 and 11 show one example of the usage pattern of the fundus oculi observation device 1. The usage pattern shown in these flowcharts is for automation of alignment of the measurement position in the depth direction of the fundus oculi Ef. A process shown in the flowchart of FIG. 10 is a process in a preparation stage for capturing an OCT image of the fundus oculi Ef. Further, a process shown in the flowchart of FIG. 11 is actual measurement of an OCT image of the fundus oculi Ef.

Preparation Stage: FIG. 10

(Step 1)

First, the controller 210 controls the reference mirror driving mechanism 243 to place the reference mirror 174 at the predetermined initial position (S1). This initial position is previously set. In this embodiment, the reference mirror 174 is moved to a position where the optical path length of the reference light LR becomes the shortest. In other words, the reference mirror 174 is placed in the position closest to the optical coupler 162 within the movable range of the reference mirror 174.

(Step 2)

Next, measurement for capturing an OCT image is performed (S2). A specific example of this process will be described below. First, the controller 210 controls the low-coherence light source 160 to output the low-coherence light L0, and also controls the mirror driving mechanisms 241 and 242 to scan with the signal light LS. The reference light LR passed through the reference mirror 174 and the signal light LS passed through the fundus oculi Ef are superimposed by the optical coupler 162, whereby the interference light LC is generated. The interference light LC is split by the diffraction grating 182, and each spectrum is detected by the CCD 184. The CCD 184 transmits detection signals to the arithmetic control unit 200. This process is performed with respect to one scanning line Ri, for example (i.e., this process is performed with respect to n number of scanning points Ri1 to Rin).

(Step 3)

Subsequently, the image forming part 220 forms an OCT image based on the detection signals inputted from the CCD 184 (S3). At this time, it is possible to shorten the processing time by performing a process as described below, for example.

First, the image forming part 220 takes out detection signals at a predetermined number of scanning points from the n number of detection signals inputted from the CCD 184. The number of the detection signals to be taken out is determined beforehand, for example, to be approximately ten.

Furthermore, the image forming part 220 forms an image Gij (OCT image) of the depth direction based on the respective detection signals having been taken out. Consequently, the predetermined number of images of the depth direction can be captured.

(Step 4)

Next, the signal-level calculator 232 calculates the signal level of the OCT image formed by the image forming part 220 (S4). Then, the signal-level calculator 232 calculates, for example, the signal level of the image of each depth direction formed in Step 3.

(Step 5)

Next, the signal-level determining part 233 determines whether the signal level calculated by the signal-level calculator 232 exceeds a threshold value (S5). Then, the signal-level determining part 233 determines, for example, whether the signal level of an image of each depth direction calculated in Step 4 exceeds the threshold value, and determines as "Y" when the signal levels of all the depth images exceed the threshold value. The determination as "Y" may also be made when a predetermined number of signal levels exceed the threshold value among a plurality of images of the depth direction.

Herein, the fact that the signal level exceeds the threshold value is equivalent to the fact that a tomographic image of the fundus oculi Ef is included within a frame of the OCT image. On one hand, the fact that the signal level is under the threshold value means that the image of the fundus oculi Ef is not included within the frame of the OCT image. Even in a case in which the tomographic image of the fundus oculi Ef is included within the frame of the OCT image, it is not clear at this stage whether this tomographic image is placed in a favorable position (e.g., a position with favorable measurement sensitivity) within the frame.

(Step 6)

When it is determined that the signal level is under the threshold value in Step 5 (S5; N), the controller 210 controls the reference mirror driving mechanism 243 to move the reference mirror 174 by a specified distance (S6). The specified distance is set in advance.

In this embodiment, the position where the optical path length of the reference light LR becomes the shortest is the initial position of the reference mirror 174 (refer to Step 1), and therefore, the reference mirror 174 is moved in a manner that the optical path length of the reference mirror LR is longer by the specified distance. When the reference mirror 174 is moved by the specified distance, the processing returns to S2, and the process up to Step 5 is executed again. Thus, until the result of determination in step 5 becomes "Y," the process from Step 2 through Step 5 is repeated. In other words, until a tomographic image of the fundus oculi Ef shows up within the frame of the OCT image, such an action is made to gradually change the optical path length of the reference light LR by a specified distance.

(Step 7)

In a case where it is determined in Step 5 that the signal level exceeds the threshold value (S5; Y), the image-position specifying part 234 specifies the position within the frame of a predetermined partial image of each OCT image (S7).

(Step 8)

Subsequently, the movement-distance calculator 235 calculates the distance of movement of the reference mirror 174, based on the position within the frame of the partial image specified in Step 7 (S8).

(Step 9)

The controller 210 moves the reference mirror 174 by the movement distance calculated in Step 8 (S9). Thus, the depth position of the fundus oculi Ef equivalent to the partial image and the specific position within the frame coincide.

(Step 10)

When movement of the reference mirror 174 in step 9 is finished, the examiner operates an operation part 240B (for example, an imaging switch 306) to request start of measurement of an OCT image (tomographic image) of the fundus oculi Ef. The controller 210 controls a low-coherence light source 160, mirror driving mechanisms 241 and 242, and so on, to start actual measurement of the OCT image (S10).

[Actual Measurement: FIG. 11]

(Step 11)

When actual measurement is started, the controller 210 causes a display 240A to display a tomographic image Gk along a certain scan line Rk (k=1 through m). At this moment, the controller 210 makes a signal light LS repeatedly scan along the scan line Rk, and updates a displayed image of the tomographic image Gk in real time. The examiner checks the position of the tomographic image Gk within a frame. When necessary, the examiner adjusts the position of the reference mirror 174 so that the tomographic image Gk is located in a desired position within the frame.

(Step 12)

Next, the examiner operates the operation part 240B to start fixation of the depth position of the tomographic image (S12). Consequently, a position within the frame of a tomographic image to be obtained is set. This position is set to, for example, a position (z-axis value) of a partial image corresponding to a predetermined layer of the fundus oculi Ef within the tomographic image Gk displayed in step 11. The position thus set is one example of the "specific position" of the present invention.

(Step S13)

Subsequently, measurement for one scan line is performed (S13). In other words, the controller 210 controls the low-coherence light source 160, the mirror driving mechanisms 241 and 242, and so on, to sequentially apply the signal light LS to scan points R1 through R1n on a first scan line R1. A CCD 184 sequentially detects an interference light LC based on the signal light LS applied to each of the scan points R11 through R1n, and sends detected signals to the image forming part 20.

(Step 14)

The image forming part 220 forms images G11 through G1n in the depth direction at the respective scan points R11 through R1n based on the detection signals sequentially inputted from the CCD 184, and aligns the images G11 through G1n, thereby forming a tomographic image G1 along the scan line R1 (S14).

(Step 15)

Here, it is determined by the controller 210 whether measurement of the fundus oculi Ef is completed or not (S15). In this usage pattern, it is determined that "measurement is completed" when measurement on m lines of scan lines R1 through Rm is completed (S15; Y).

(Step 16)

In a case where measurement is not completed (S15; N), an image-position specifying part 234 specifies the position within the frame of the aforementioned partial image in an image Gij in each of the depth directions along the scan lines Ri (i=1 through m-1) (S16). Here, by taking out a predetermined number of images from among n pieces of images Gij in the depth direction along the scan lines Ri, and specifying the position of the partial image within in the frame only for each of the predetermined number of images, process time may be shortened.

(Step 17)

Subsequently, a movement-distance calculator 235 calculates a movement distance of the reference mirror 174 based on the position within the frame of the specified partial image in step 16 (S17).

(Step 18)

The controller 210 moves the reference mirror 174 by the movement distance calculated in step 17 during line switching scan r shown in FIG. 8A (S18).

Describing more specifically, the controller 210 synchronizes operation timing of the low-coherence light source 160 and the mirror driving mechanisms 241 and 242 with operation timing of a reference mirror driving mechanism 243, thereby fixes the position of the reference mirror 174 while making the signal light LS scan along the scan line R1, and moving the reference mirror 174 while scan along the line switching scan r is performed.

Accordingly, it is possible to favorably measure at the respective scan points Rij in a state where the position of the reference mirror 174 is fixed, and it is possible to change the position of the reference mirror 174 during line switching scan r in which measurement is not performed (namely, during movement of position of signal light LS).

After movement of the reference mirror 174, measurement for the next scan line R (i+1) is performed (S13). Thus, until determination "N" is made in step 15, measurement for the m lines of scan lines R1 through Rm is performed to acquire the m pieces of tomographic images G1 through Gm. This is the end of the description of the usage pattern shown in FIGS. 10 and 11.

(Modification of Usage Pattern)

In addition, for example, when the movement distance of the reference mirror 174 calculated in step 17 is comparatively long, or when the movement speed of the reference mirror 174 is comparatively slow, it may be impossible to move the reference mirror 174 by a target distance during single line switching scan r. In these cases, by employing such a configuration as described below, it is possible to move the reference mirror 174 by a target distance.

The reference-mirror driving mechanism 243 is configured to have, as an actuator, a pulse motor (stepping motor) that operates in response to a pulse signal from the controller 210. Moreover, the reference-mirror driving mechanism 243 is configured to move the reference mirror 174 by a predetermined unit distance in response to a single pulse signal. Besides, the hard disk drive 204 or the like is configured to previously store the relation (relational information) between a pulse number (a number of pulse signals) and a movement distance.

In step 18, the controller 210 sends a predetermined pulse number of pulse signals to the reference-mirror driving mechanism 243. The reference-mirror driving mechanism 243 moves the reference mirror 174 by a distance corresponding to the pulse number during single line switching scan r.

The movement-distance determining part 211 finds a movement distance d1 of the reference mirror 174 during single line switching scan r, based on the number of the pulses sent to the reference mirror 174 and the relational information. Further, the movement-distance determining part 211 determines the magnitude relation between the movement distance d1 and the movement distance (target movement distance) calculated in step 17. When the actual movement distance d1 and the target movement distance are equal, the controller 210 executes the process in accordance with FIG. 11 described above.

On the other hand, when the actual movement distance d1 is shorter than the target movement distance, the controller 210 sends more pulse signals to the reference-mirror driving mechanism 243. The reference-mirror driving mechanism 243 moves the reference mirror 174 by a distance corresponding to the number of the pulse signals during the next line switching scan r.

The movement-distance determining part 211 finds a movement distance d2 of the second movement, and calculates a sum d1+d2 of the movement distances found so far. Then, the movement-distance determining part 211 determines the magnitude relation between the sum d1+d2 of the movement distances and the target movement distance.

This process is repeatedly executed until the sum of the movement distances becomes equal to the target movement distance. Thus, it is possible to move the reference mirror 174 by the target movement distance during plural times of line switching scan r.

Otherwise, it is also possible to configure so as to, instead of finding the actual movement distance of the reference mirror 174 based on the number of pulses sent to the pulse motor as described above, obtain the actual movement distance of the reference mirror 174 by detecting the position and movement distance of the reference mirror 174 by using a potentiometer and an encoder such as a rotary encoder.

Further, it is also possible to configured so as to, instead of comparing the actual movement distance with the target movement distance every time the reference mirror 174 is moved, execute movement control of the reference mirror 174 after determining the number of times to move the reference mirror 174 based on the target movement distance calculated in step 17 and the movement distance (unit movement distance) during single line switching scan r.

SPECIFIC EXAMPLE

A specific example of the usage pattern of the fundus oculi observation device 1 described thus far will be described with reference to FIG. 12 through FIG. 14.

Figure 12:
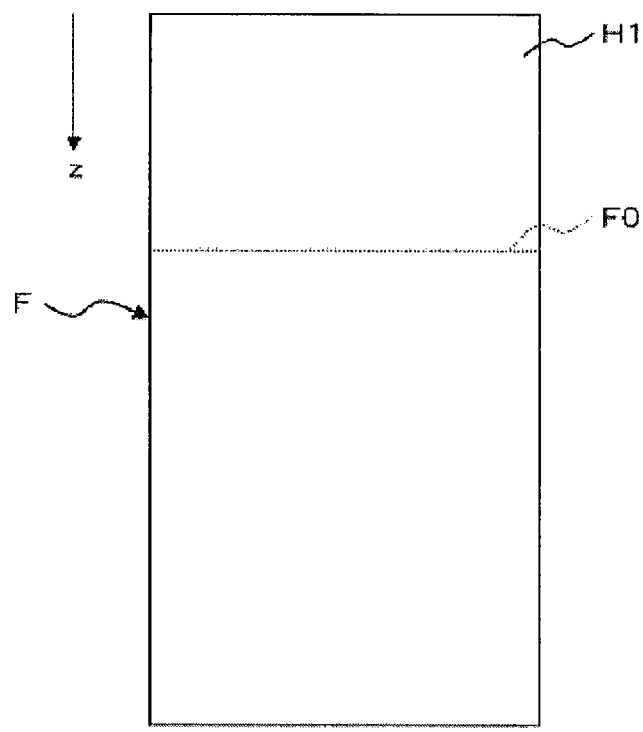
FIG. 12 is a schematic explanation view for explaining a specific example of the usage pattern in the preferred embodiment of the device related to the present invention.

When an OCT image is captured in a case where the determination result in Step 5 of the above usage pattern is "N," an OCT image H1 as shown in FIG. 12 is acquired. The OCT image H1 is formed within a frame F, but a tomographic image of the fundus oculi Ef is not included within the frame F. In this case, since the depth position corresponding to the position of the reference mirror 174 exists within the vitreous body, the tomographic image of the fundus oculi Ef does not show up within the frame F.

Reference symbol F0 in FIG. 12 denotes a specific position within the frame F described in the process for calculating the movement distance of the reference mirror 174. In the frame F shown in FIG. 12, measurement sensitivity is favorable on the side with a smaller z coordinate value (i.e., the upper side of the paper in FIG. 12). This is because the initial position of the reference mirror 174 corresponds to the side with a smaller z coordinate value as described in Step 1.

Figure 13:
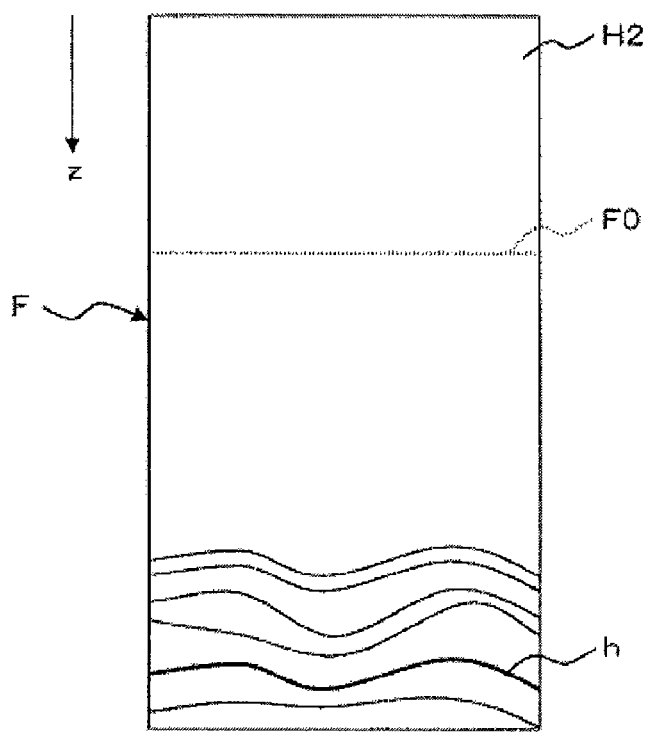
FIG. 13 is a schematic explanation view for explaining a specific example of the usage pattern in the preferred embodiment of the device related to the present invention.

When an OCT image is captured when the determination result in Step 5 is "Y," an OCT image H2 as shown in FIG. 13 is acquired. This OCT image H2 is formed within the frame F, and includes a tomographic image of the fundus oculi Ef in a region on a side where the z coordinate value within the frame F is greater (i.e., lower side of the paper in FIG. 13). Reference symbol h within FIG. 13 denotes a layer of the fundus oculi Ef equivalent to the above-described partial image with the greatest pixel value.

The OCT image H2 shown in FIG. 13 includes the tomographic image of the fundus oculi Ef, but this tomographic image is displayed in a region within the frame F where measurement sensitivity is not favorable. In the above usage pattern, a tomographic image is to be displayed in a region within the frame F with favorable measurement sensitivity by the process from Step 7 through Step 9.

That is to say, the position within the frame F of a partial image equivalent to the layer h of the OCT image H2 is specified in Step 7, and the movement distance of the reference mirror 174 is found in Step 8 by calculating the displacement between the z coordinate value of the layer h and the z coordinate value of the specific position F0. Then, in Step 9, the reference mirror 174 is moved by the movement distance.

Figure 14:
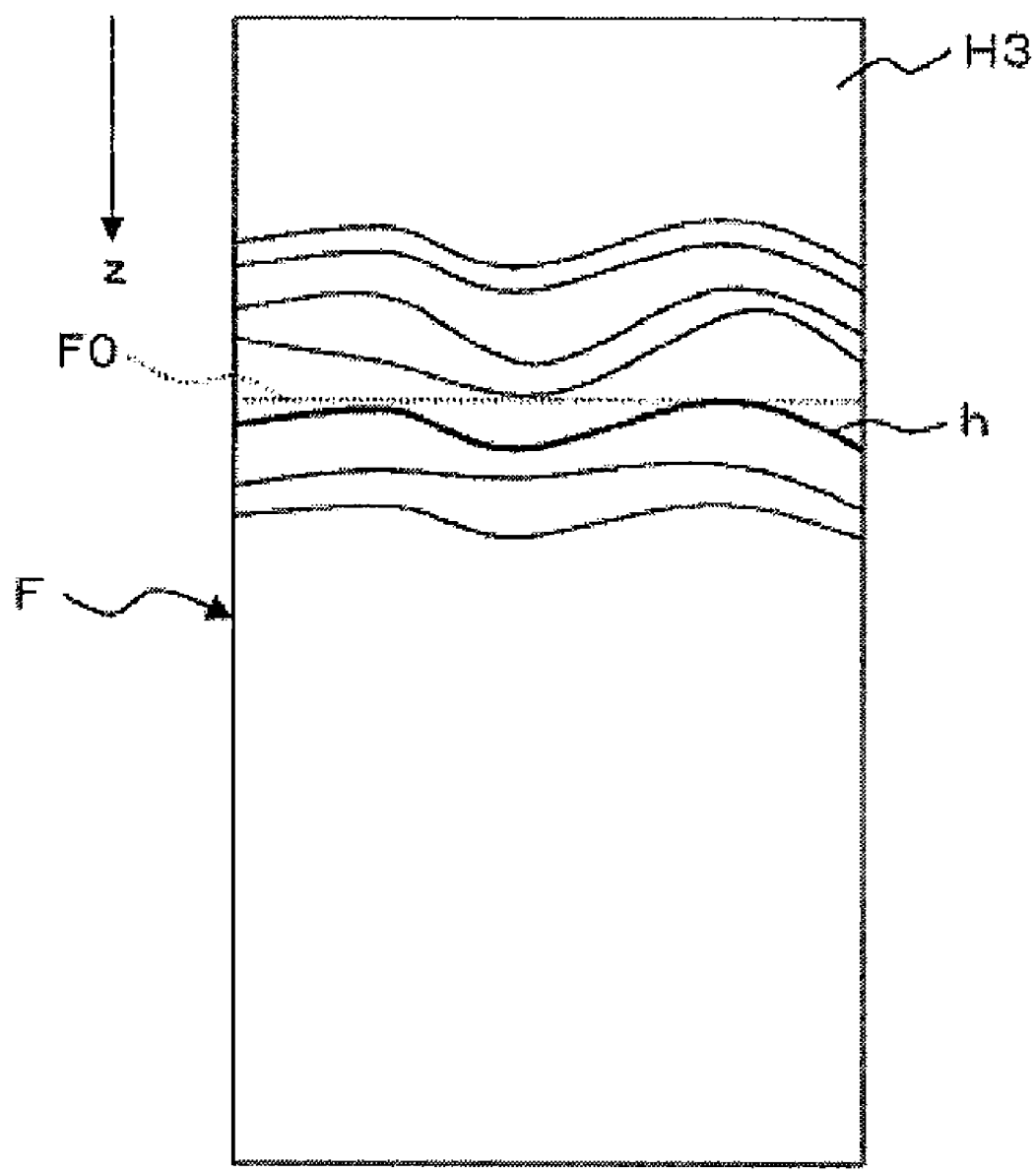
FIG. 14 is a schematic explanation view for explaining a specific example of the usage pattern in the preferred embodiment of the device related to the present invention.

By conducting such a process, a tomographic image of the fundus oculi Ef is displayed in a manner that the layer h is placed in the specific position F0 within the frame F, like an OCT image H3 shown in FIG. 14. As described above, the specific position F0 is set in a position within the frame F where the measurement sensitivity is favorable. Therefore, the tomographic image in the OCT image H3 is clearly displayed in comparison with the tomographic image within the OCT image H2 of FIG. 13.

Thus, an OCT image displayed in step 11 becomes such that, like the OCT image H3 of FIG. 14, the layer h is located at the specific position F0 within the frame F or the layer h is located in the vicinity of the specific position F0. That is, an examination with the fundus oculi observation device 1, as well as the conventional fundus camera, can be performed in a state where the face of a subject is fixed and placed with a forehead rest, a jaw holder or the like, so that it is possible to prevent the eye E from largely moving. However, the measurement depth may shift because of movement of the fundus oculi Ef in the Z direction resulting from the blood flow or the like.

The process shown in FIG. 11 is to perform new measurement so that an OCT image is located at a favorable position within the frame F in this manner. In other words, this process is to perform new measurement so as to locate an OCT image at the specific position F0 within the frame F as well as the OCT image displayed in step 11. Consequently, according to actual measurement of the usage pattern described above, it is possible to capture m pieces of OCT images (tomographic images G1 through Gm) that the layer h is located at or in the vicinity of the specific position F0 within the frame F.

[Another Usage Pattern]

Figure 15:
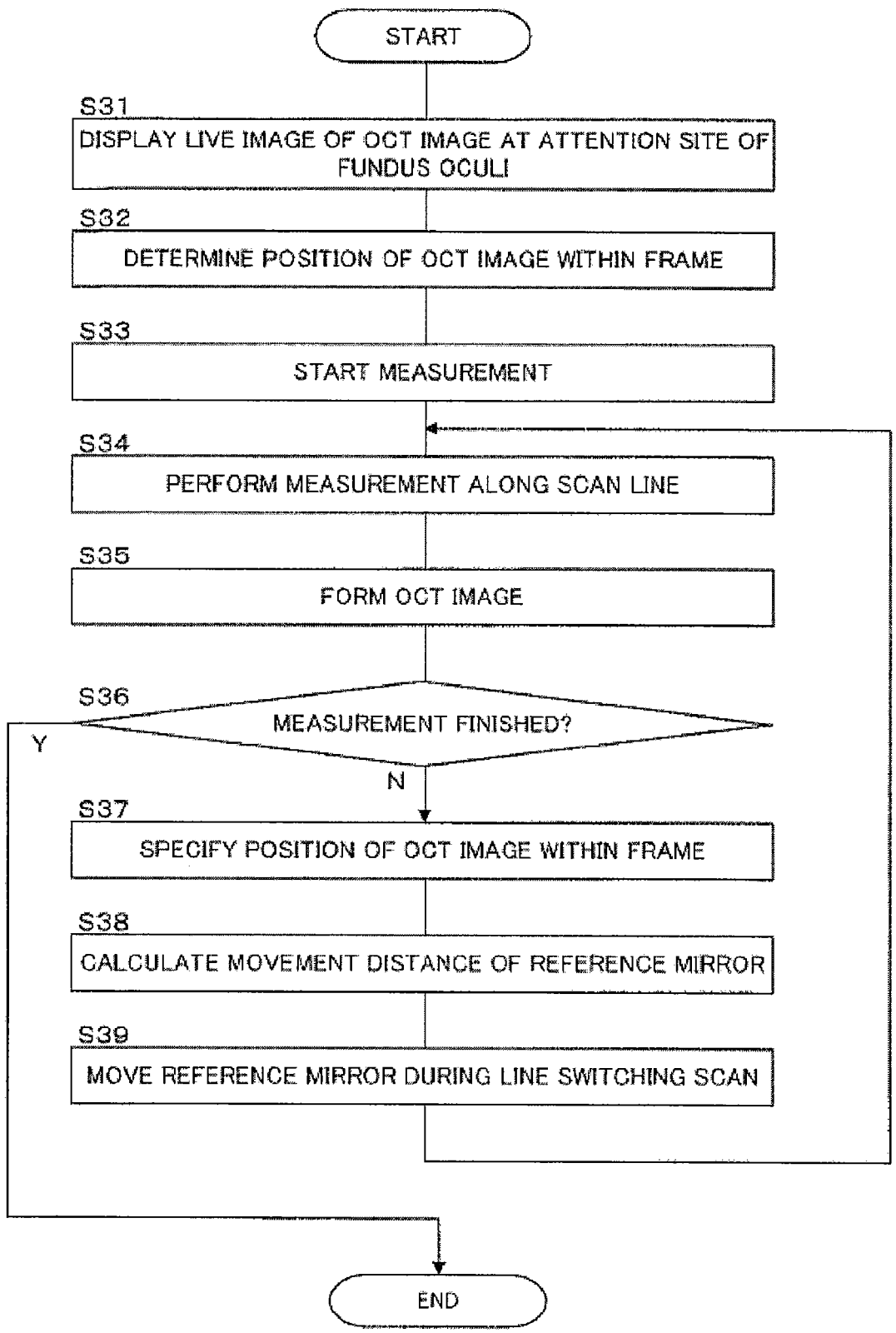
FIG. 15 is a flowchart showing one example of a usage pattern in the preferred embodiment of the device related to the present invention.

Another usage pattern of the fundus oculi observation device 1 relating to this embodiment will be described referring to a flowchart of FIG. 15.

In this usage pattern, a process of correcting a deviation in the depth direction of a measurement position resulting from the surface of the fundus oculi Ef being a curved face, that is, a process of correcting displacement of an OCT image within the frame will be described.

Figure 16:
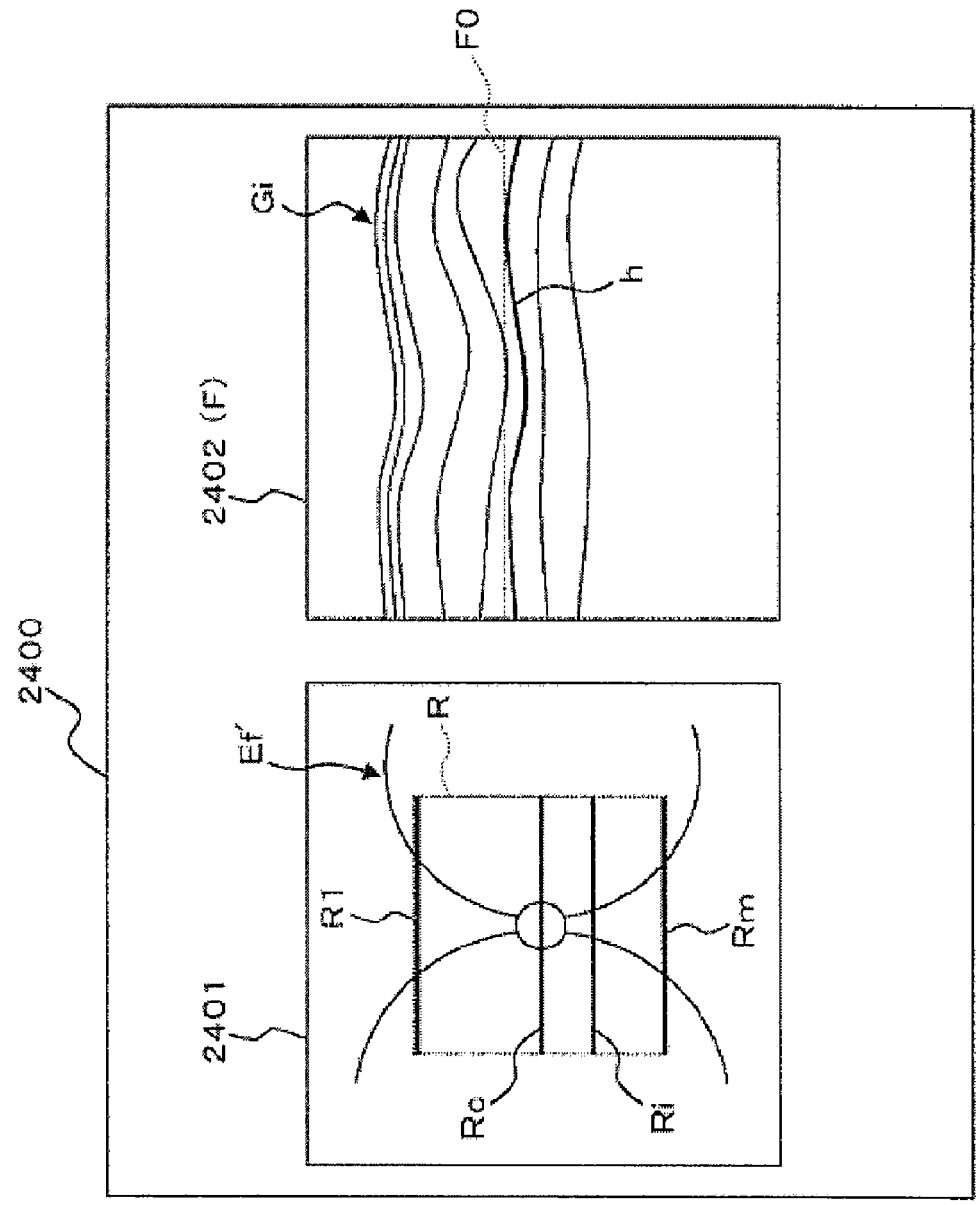
FIG. 16 is a schematic explanation view for explaining one example of the usage pattern in the preferred embodiment of the device related to the present invention.
Figure 17:
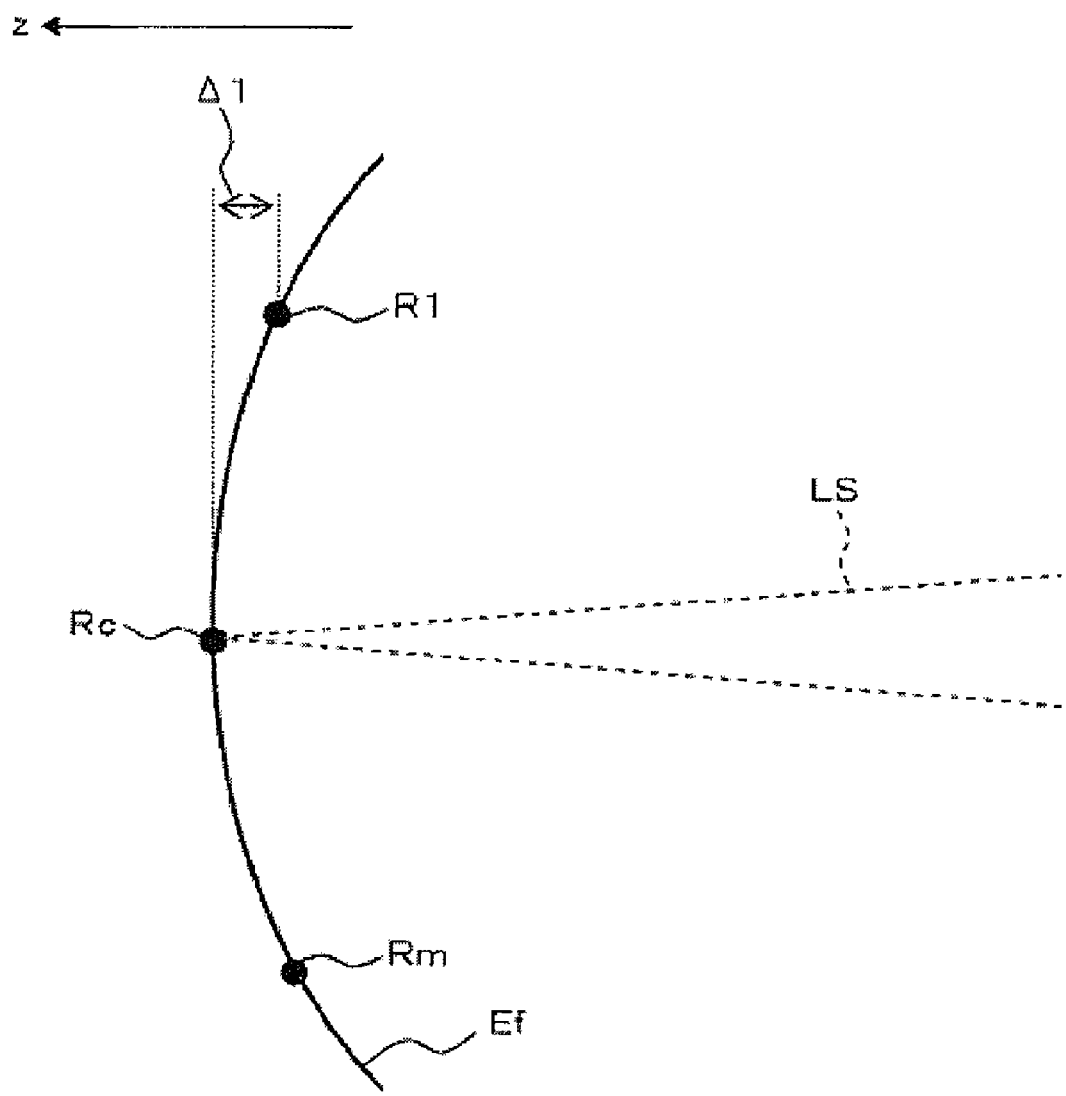
FIG. 17 is a schematic explanation view for explaining one example of the usage pattern in the preferred embodiment of the device related to the present invention.

Here, FIG. 16 shows a scan region R set on the fundus oculi image Ef'. In this scan region R, a plurality of scan lines Ri are set (refer to FIG. 8A). Further, FIG. 17 is a side cross-sectional view of the fundus oculi Ef.

A process at the preparation stage before the process shown in FIG. 15 will be described. First, the fundus oculi image Ef' is captured, and displayed on the display 240A. The fundus oculi image Ef' is displayed on a fundus oculi image display 2401 of a display screen 2400 of the display 240A.

Next, the examiner sets a region (scan region R) to obtain an OCT image while observing the displayed fundus oculi image Ef'. The scan region R is set so that a central position thereof is located at the center of the optic papilla (a part shown as a circle in the fundus oculi image Ef' of FIG. 16) of the fundus oculi Ef. In addition, reference numeral Rc shown in FIG. 16 denotes a scan line passing through the central position of the optic papilla of the scan lines R1 through Rm. The following is a description of the process shown in FIG. 15.

The examiner operates the operation part 240B to specify the central position (attention site) of the optic papilla on the fundus oculi image Ef'. The controller 210 selects the scan line Rc passing through the specified position, and makes the signal light LS repeatedly scan along the scan line Rc. The controller 210 makes a tomographic image Gc (not shown) sequentially obtained through repeated scan updated and displayed in real time. The tomographic image Gc is displayed on an OCT image display 2402 of the display screen 2400. Thus, a live image of the tomographic image Gc at the position of the scan line Rc is displayed (S31).

A display range of the OCT image display 2402 is set to the same range as the frame F. However, in the case of magnified display of an OCT image, only an image of a partial range within the frame F is displayed on the OCT image display 2402.

Next, the examiner operates the operation part 240B to determine the position of the OCT image within the frame F (S32). For this, the examiner regulates the position of the reference mirror 174 while checking the position of the tomographic image Gc displayed on the OCT image display 2402, thereby making the tomographic image Gc displayed at a desired position within the OCT image display 2402. Here, regulation of the position is performed so that a predetermined partial image (the layer h, the fundus oculi surface or the like) of the tomographic image Gc is located at the specific position F0.

At this moment, the regulation of the position may be assisted by displaying information representing the position of the specific position F0 on the OCT image display 2402. Further, adjustment of the position of the OCT image may be performed automatically in the same manner as in the aforementioned usage pattern.

After the adjustment of the position of the OCT image, the examiner performs a predetermined operation to start measurement (S33). In response thereto, the controller 210 controls the mirror driving mechanisms 241 and 242 to move an application position of the signal light LS onto the first scan line R1 (on the first scan point R11). Then, the controller 210 controls the low-coherence light source 160 and the mirror driving mechanisms 241 and 242 to make the signal light LS sequentially scan on the respective scan points R11 through R1n on the scan line R1. The interference light LC based on each of the signal light LS is detected by the CCD 184.

The image forming part 220 forms images Gi1 through G1n in the depth direction at the respective scan points R11 through R1n, and forms a tomographic image G1 (S35).

Here, the controller 210 determines whether measurement for the scan lines R1 through Rm has finished or not (S36).

In a case where the measurement has not finished (S36; N), the image-position specifying part 234 takes out a predetermined number of images from the n pieces of images Gij in the depth direction along the scan line Ri (i=1 through m-1), and specifies the position within the frame F of the layer h in the predetermined number of images. Consequently, the position of the tomographic image G1 within the frame F is specified (S37).

Subsequently, the movement-distance calculator 235 calculates a movement distance of the reference mirror 174 based on the position within the frame F of the layer h specified in step 37 (S38).

The controller 210 moves the reference mirror 174 by the movement distance calculated in step 38 while line switching scan r is performed (S39). By repeatedly executing the above process until determination "Y" is made in step S36, it is possible to capture the tomographic images G1 through Gm corresponding to the scan lines R1 through Rm.

In this usage pattern, when the application position of the signal light LS is moved from the scan line Rc to the scan line R1, a deviation of the measurement position in the depth direction is made. That is, since a displacement Δ1 in the z direction exists between the scan line Rc and the scan line R1 as shown in FIG. 17, a difference about the displacement Δ1 is made between the measurement depth at the scan line Rc and the measurement depth at the scan line R1.

Further, although being slight, a displacement in the z direction exists also between the scan line Ri (i=1 through m-1) and the scan line R(i+1), a slight deviation is made between the measurement depth at the scan line Ri and the measurement depth at the scan line R (i+1).

According to this usage pattern, it is possible to capture the tomographic images G1 through Gm while correcting a deviation of the measurement depth resulting from the fundus oculi Ef having a curved shape.

Although a deviation of the measurement depth is corrected based on the position within the frame F of the actually obtained OCT image in this usage pattern, it is also possible to configure so as to correct the deviation based on a displacement of the measurement depth obtained previously. For example, in a case where the radius of curvature of the fundus oculi Ef is already known, it is possible to calculate the displacement of the measurement depth from the radius of curvature. Further, in a case where the OCT image of the fundus oculi Ef was captured in the past, it is possible to calculate the displacement of the measurement depth based on the past OCT image.

[Advantageous Effects]

Actions and advantageous effects of the fundus oculi observation device 1 as described above will be described below.

The fundus oculi observation device 1 functions as an optical image measurement device capable of measuring an OCT image such as a tomographic image of the fundus oculi Ef. This fundus oculi observation device 1 is configured to specify the position of the OCT image within the frame F and, based on the specified position, change the position of the reference mirror 174 so that a newly formed OCT image is located at a predetermined position within the frame F.

Thus, according to the fundus oculi observation device 1, it is possible to capture an OCT image located at a predetermined position within the frame F, it is possible to capture an image in a target depth position of the fundus oculi Ef (measurement object).

Here, the predetermined position within the frame F is, in the above embodiment, such a position of the tomographic image Gi that the layer h is located at the specific position F0, and generally a position within the frame F in which the measurement object can be measured with comparatively high sensitivity. This layer h is a partial image corresponding to the predetermined depth position of the fundus oculi Ef.

Further, since the fundus oculi observation device 1 is configured so as to move the reference mirror 174 only when the application position of the signal light LS by the scan unit 141 is being moved, it is possible to securely perform measurement for the respective scan points Rij in a state where the position of the reference mirror 174 is fixed, and it is possible to correct the depth position of measurement for capturing the tomographic images G1 through Gm. Specifically, the fundus oculi observation device 1 is configured to make the signal light LS scan along a plurality of scan lines Ri set in advance, and move the reference mirror 174 only when the application position of the signal light LS is being moved from one scan line to another scan line of the scan lines Ri.

Further, the fundus oculi observation device 1 is configured to calculate a movement distance of the reference mirror 174 for locating a newly formed OCT image at a predetermined position and, when the actually moved distance is shorter than the calculated distance, further move the reference mirror 174 during movement of the application position of the signal light LS for the next time and later, thereby moving the reference mirror 174 by the calculated distance. Consequently, even if the fundus oculi Ef has largely moved in the depth direction, or even if the movement speed of the reference mirror 174 is low, it is possible to capture an OCT image in a target depth position.

Further, the fundus oculi observation device 1 is configured to sequentially move an application position of the signal light LS to the plurality of scan points Rij on the scan line Ri and detect the interference light LC based on the signal light LS applied to each of the scan points Rij, and specify positions within the frame F of the images Gij of the depth direction based on a predetermined number of detection results of the interference light LC and move the reference mirror 174 based on these specified positions so that a new OCT image is located at a predetermined position within the frame F. Consequently, it is possible to shorten a process time for capturing an OCT image at a target depth position, and it is possible to correct a depth position in (almost) real time for every scan line Ri, for example.

Further, the fundus oculi observation device 1 is configured to calculate the signal level of a formed OCT image and move the reference mirror 174 when the signal level exceeds a threshold, and move the reference mirror 174 so that a newly formed OCT image is located at a predetermined position. Consequently, it is possible to automatically correct the depth position so that the OCT image appears within the frame F in a case where the OCT image does not appear within the frame F at the initial stage, and it is also possible to correct the depth position so that the OCT image is located at a predetermined position within the frame F.

According to the present invention, by analyzing an image formed by an image forming part, specifying the position of the image within a predetermined frame, and controlling a changer based on the specified position, it is possible to change a difference in optical path length so that an image of a measurement object newly formed by the image forming part is located at a predetermined position within the predetermined frame. Accordingly, by setting the predetermined position within the frame as a position corresponding to a target depth position of the measurement object, it is possible to capture an image of the target depth position of the measurement object.

Here, the predetermined position within the frame can be set to, for example, a position in which a target depth position of a measurement object can be measured with high sensitivity.

[Modification]

The configuration described above is merely a specific example for favorably implementing the present invention. Therefore, it is possible to properly make any modification within the scope and intent of the present invention.

For example, in the embodiment described above, the difference between the light path of a signal light and the light path of a reference light (difference in optical path length) is changed by changing the position of the reference mirror 174, but the method for changing the difference in optical path length is not limited to this. For instance, it is possible to change the difference in optical path length by integrally moving the retinal camera unit 1A and the OCT unit 150 with respect to the eye E and changing the optical path length of the signal light LS. Furthermore, it is also possible to change the difference in optical path length by moving a measurement object in a depth direction (z-direction). In general, as the "changer" in the present invention, it is possible to employ any constitution for changing the difference in optical path length between the signal light and reference light.

Further, in the above embodiment, a difference in optical path length between signal light and reference light is changed during line switching scan r (namely, during change of a scan line), but timing to change the difference in optical path length is not limited thereto. For example, it is possible to change the difference in optical path length while moving the application position of the signal light LS from a certain scan point to the next scan point. In general, it is possible to change a difference in optical path length between signal light and reference light at any timing when measurement for forming an OCT image is not performed actually, such as when the low-coherence light source 160 is not turned on, when the signal light LS is not applied to a measurement object, and when the CCD 184 is not detecting the reference light LC.

Moreover, in the embodiment described above, a state where the optical path length of the reference light is shortest is assumed to be an initial state and a state where the signal level exceeds the threshold value is searched, but it is also possible to configure so that any state such as a state where the light path length of the reference light is the longest is assumed to be an initial state and a target state is searched.

Furthermore, in the embodiment described above, a state where the signal level exceeds the threshold value is searched while gradually increasing the optical path length of the reference light, but it is also possible to configure so that the target state is searched while gradually decreasing the optical path length of the reference light. Moreover, it is also possible to configure so as to pursue the target state by increasing and decreasing the optical path length of the reference light. In addition, instead of changing the optical path length of the reference light, it is also possible to configure so as to search the target state by gradually increasing (or decreasing) the optical path length of the signal light or pursue the target state by increasing and decreasing the optical path length of the signal light.

Moreover, in the embodiment described above, the position of an image of the measurement object within a frame is determined based on the signal level of an OCT image, but it is also possible to configure so that the position of the image is determined based on the ratio of signal level and noise level (S/N ratio).

Calculation of the S/N ratio of an OCT image is conducted by an analyzing part 231 (analyzer). Furthermore, it is possible to employ any known method as a method for calculating the S/N ratio. Moreover, the OCT image to be subjected to calculation of the S/N ratio may be a 2-dimensional tomographic image, or may be a 1-dimensional image of a depth direction.

By thus considering the S/N ratio, it is possible to increase the accuracy in determining the image position. In particular, it may be desired to consider the S/N ratio, for example, when the amount of noise contained in an OCT image is large or noise cannot be removed effectively due to the state of the measurement object or the device.

The fundus oculi observation device described in the above embodiment is comprises an optical image measurement device of Fourier domain type, but it is also possible to apply the configuration of the present invention to an optical image measurement device of Time Domain type. The time domain type of optical image measurement device is described in, for example, Japanese Unexamined Patent Application Publication 2005-241464. Moreover, it is also possible to apply the configuration of the present invention to an optical image measurement device of any other type such as a Swept Source type.

[Program]

A program configured to control the device according to the present invention will be explained hereunder. In the above embodiments, the control program 204a is equivalent to the program.

This program causes an optical image measurement device to function as an analyzer and controller as described later. The optical image measurement device comprises: a light source configured to emit a low-coherence light; an interference-light generator configured to split the emitted low-coherence light into a signal light traveling to a measurement object and a reference light traveling to a reference subject; a changer configured to change a difference in optical path length between the signal light and the reference light; a detector configured to detect the generated interference light;

and an image forming part configured to form an image of the measurement object within a predetermined frame based on a result of the detection. The analyzer analyzes the image formed by the image forming part and specifies the position of the image within the predetermined frame. The controller controls the changer based on the position specified by the analyzer to change the difference in optical path length so that an image of the measurement object newly formed by the image forming part is located at a predetermined position within the predetermined frame.

According to this program, it is possible to capture an image located at a predetermined position within a predetermined frame, so that it is possible to capture an image at a target depth position of a measurement object.

This program can be stored in any recording medium readable by a drive of the computer. For example, a storing medium such as an optical disk, a magneto-optical disk (CD-ROM, DVD-ROM, DVD-ROM, MO, etc.) and a magnetic storing medium (hard disk, floppy disk™, ZIP, etc.) can be used. Moreover, it is also possible to store the program in a storage device such as a hard disk drive or a memory. Furthermore, it is also possible to transmit the program via a network such as the Internet and a LAN.

What is claimed is:

1. An optical image measurement device, comprising:
a light source configured to emit a low-coherence light;
an interference-light generator configured to generate an interference light, by splitting the emitted low-coherence light into a signal light heading toward a measurement object and a reference light heading toward a reference object, and superimposing the signal light passed through the measurement object and the reference light passed through the reference object;
a changer configured to change a difference in optical path length between the signal light and the reference light;
a detector configured to detect the generated interference light;
an image forming part configured to form an image of the measurement object within a predetermined frame based on the result of the detection by the detector;
an analyzer configured to analyze the formed image, and specify a position within the predetermined frame of a partial image of the formed image corresponding to a predetermined depth position of the measurement object; and
a controller configured to control the changer based on the specified position to change the difference in optical path length so that, in a newly formed image by the image forming part, the partial image is placed in a specific position within the predetermined frame, thereby placing the newly formed image in a predetermined position,
wherein regarding the formed image, the analyzer finds the position of the partial image within the predetermined frame, and calculates displacement between the found position and the specific position; and
the controller controls to change the difference in optical path length by a distance corresponding to the displacement, thereby placing the partial image of the newly formed image in the specific position.

2. An optical image measurement device, comprising:
a light source configured to emit a low-coherence light;
an interference-light generator configured to generate an interference light, by splitting the emitted low-coherence light into a signal light heading toward a measurement object and a reference light heading toward a reference object, and superimposing the signal light passed through the measurement object and the reference light passed through the reference object;
a scanner configured to move an application position of the signal light to the measurement object;
a changer configured to change a difference in optical path length between the signal light and the reference light;
a detector configured to detect the generated interference light;
an image forming part configured to form an image of the measurement object within a predetermined frame based on the result of the detection by the detector;
an analyzer configured to analyze the formed image, and specify a position of the image within the predetermined frame; and
a controller configured to control the changer based on the specified position to change the difference in optical path length only while the scanner is moving the application position so that an image of the measurement object newly formed by the image forming part is placed in a predetermined position within the predetermined frame,
wherein the analyzer calculates a change distance of the difference in optical path length for placing the newly formed image in the predetermined position; and
in a case where the difference in optical path length changed while movement of the application position is shorter than the change distance, the controller controls to further change the difference in optical path length while next or later movement of the application position by the scanner, thereby changing the difference in optical path length by the change distance.

3. An optical image measurement device, comprising:
a light source configured to emit a low-coherence light;
an interference-light generator configured to generate an interference light, by splitting the emitted low-coherence light into a signal light heading toward a measurement object and a reference light heading toward a reference object, and superimposing the signal light passed through the measurement object and the reference light passed through the reference object;
a scanner configured to move an application position of the signal light to the measurement object;
a changer configured to change a difference in optical path length between the signal light and the reference light;
a detector configured to detect the generated interference light;
an image forming part configured to form an image of the measurement object within a predetermined frame based on the result of the detection by the detector;
an analyzer configured to analyze the formed image, and specify a position of the image within the predetermined frame; and
a controller configured to control the changer based on the specified position to change the difference in optical path length only while the scanner is moving the application position so that an image of the measurement object newly formed by the image forming part is placed in a predetermined position within the predetermined frame,
wherein the scanner scans with the signal light along a plurality of preset scan lines, and
the controller controls to change the difference in optical path length only while the application position is being moved from one of the plurality of scan lines to another.

4. An optical image measurement device, comprising:

a light source configured to emit a low-coherence light;

an interference-light generator configured to generate an interference light, by splitting the emitted low-coherence light into a signal light heading toward a measurement object and a reference light heading toward a reference object, and superimposing the signal light passed through the measurement object and the reference light passed through the reference object;

a scanner configured to move an application position of the signal light to the measurement object;

a changer configured to change a difference in optical path length between the signal light and the reference light;

a detector configured to detect the generated interference light;

an image forming part configured to form an image of the measurement object within a predetermined frame based on the result of the detection by the detector;

an analyzer configured to analyze the formed image, and specify a position of the image within the predetermined frame; and a controller configured to control the changer based on the specified position to change the difference in optical path length only while the scanner is moving the application position so that an image of the measurement object newly formed by the image forming part is placed in a predetermined position within the predetermined frame, wherein the scanner sequentially moves the application position to a plurality of scan points on the preset scan lines;

the detector detects interference lights based on the signal light applied to each of the plurality of scan points;

for each of images of a depth direction of the measurement object formed by the image forming part based on the result of the detection of a predetermined number of interference lights of the plurality of interference lights, the analyzer specifies a position within the predetermined frame; and based on the position specified for each of the predetermined number of images of the depth position, the controller controls the changer to change the difference in optical path length so that an image newly formed by the image forming part is placed within the predetermined position.

5. An optical image measurement device, comprising:

a light source configured to emit a low-coherence light;

an interference-light generator configured to generate an interference light, by splitting the emitted low-coherence light into a signal light heading toward a measurement object and a reference light heading toward a reference object, and superimposing the signal light passed through the measurement object and the reference light passed through the reference object;

a changer configured to change a difference in optical path length between the signal light and the reference light;

a detector configured to detect the generated interference light;

an image forming part configured to form an image of the measurement object within a predetermined frame based on the result of the detection by the detector;

an analyzer configured to analyze the formed image, and specify a position of the image within the predetermined frame; and a controller configured to control the changer based on the specified position to change the difference in optical path length so that an image of the measurement object newly formed by the image forming part is placed in a predetermined position within the predetermined frame, wherein the image forming part sequentially forms an image of the measurement object within the predetermined frame, based on the detection result of the interference light sequentially detected by the detector;

the analyzer sequentially specifies a position within the predetermined frame of the sequentially formed image; and based on the sequentially specified position, the controller controls to sequentially change the difference in optical path length so that an image formed next by the image forming part is placed within the predetermined position.

* * * * *